(12) United States Patent
Pachot

(10) Patent No.: US 12,343,368 B2
(45) Date of Patent: Jul. 1, 2025

(54) ***CLEOME DROSERIFOLIA* EXTRACT AND THERAPEUTIC OR COSMETIC USE THEREOF**

(71) Applicant: ANPJ HEALTHCARE, Paris (FR)

(72) Inventor: Jean Pachot, Paris (FR)

(73) Assignee: ANPJ HEALTHCARE, Paris (FR)

( * ) Notice: Subject to any disclaimer, the term of this patent is extended or adjusted under 35 U.S.C. 154(b) by 721 days.

(21) Appl. No.: 17/622,398

(22) PCT Filed: Jun. 26, 2020

(86) PCT No.: PCT/EP2020/068070
§ 371 (c)(1),
(2) Date: Jan. 19, 2022

(87) PCT Pub. No.: WO2020/260611
PCT Pub. Date: Dec. 30, 2020

(65) Prior Publication Data
US 2022/0354912 A1    Nov. 10, 2022

(30) Foreign Application Priority Data
Jun. 27, 2019 (FR) .................. FR1907051

(51) Int. Cl.
| | | |
|---|---|---|
| *A61K 36/00* | (2006.01) | |
| *A61K 8/04* | (2006.01) | |
| *A61K 8/9789* | (2017.01) | |
| *A61K 9/00* | (2006.01) | |
| *A61K 36/185* | (2006.01) | |
| *A61K 47/10* | (2017.01) | |
| *A61K 47/22* | (2006.01) | |
| *A61K 47/38* | (2006.01) | |
| *A61P 7/04* | (2006.01) | |
| *A61P 17/02* | (2006.01) | |
| *A61P 17/04* | (2006.01) | |
| *A61P 29/00* | (2006.01) | |
| *A61P 31/02* | (2006.01) | |
| *A61P 39/06* | (2006.01) | |
| *A61Q 19/08* | (2006.01) | |
| *A61Q 19/10* | (2006.01) | |

(52) U.S. Cl.
CPC ............ *A61K 36/185* (2013.01); *A61K 8/042* (2013.01); *A61K 8/9789* (2017.08); *A61K 9/0014* (2013.01); *A61K 47/10* (2013.01); *A61K 47/22* (2013.01); *A61K 47/38* (2013.01); *A61P 7/04* (2018.01); *A61P 17/02* (2018.01); *A61P 17/04* (2018.01); *A61P 29/00* (2018.01); *A61P 31/02* (2018.01); *A61P 39/06* (2018.01); *A61Q 19/08* (2013.01); *A61Q 19/10* (2013.01); *A61K 2236/15* (2013.01); *A61K 2236/17* (2013.01); *A61K 2236/333* (2013.01); *A61K 2236/37* (2013.01); *A61K 2236/51* (2013.01); *A61K 2236/53* (2013.01); *A61K 2800/72* (2013.01)

(58) Field of Classification Search
CPC ..................................... A61K 8/042
See application file for complete search history.

(56) References Cited

PUBLICATIONS

El-Shenawy, Does Cleome droserifolia have anti-schistosomiasis mansoni activity? Revista do Instituto de Medicina Tropical de Sao Paulo, (Jul.-Aug. 2006) vol. 48, No. 4, pp. 223-228 (Year: 2006).*
Nasef, Biological investigations of a new natural recipe expected to promote healing of superficial burns: International Journal of Pharmaceutical and Clinical Research, (Aug. 1, 2016) vol. 8, No. 8, pp. 1230-1239 (Year: 2016).*
Abdel-Gawad, A., et al, "EssentialOil Composition, Antioxidant and Allelopathic Activities of *Cleome droserifolia* (Forssk.) Delile", Chemistry & Biodiversity, Dec. 1, 2018, pp. 1-9, vol. 15, No. 12.
Sharaf, M., et al., "Exudate flavonoids from aerial parts of four *Cleome* species", Biochemical Systematics and Ecology, Jul. 1, 1992, pp. 443-448, vol. 20, No. 5.
Hegazy, A., et al., "Inhibition of seed germination and seedling growth byCleome droserifolia and allelopathic effect on rhizosphere fungi in Egypt", Journal of Arid Environments, Jan. 1, 1995, pp. 3-13, vol. 29, No. 1.
Muhaidat, R., et al., "Phytochemical investigation and in vitro antibacterial activity of essential oils from *Cleome droserifolia* (Forssk.) Delile and *C. trinervia* Fresen. (Cleomaceae)", South African Journal of Botany, Jul. 1, 2015, pp. 21-28, vol. 99.

* cited by examiner

*Primary Examiner* — Qiuwen Mi
(74) *Attorney, Agent, or Firm* — Greer, Burns & Crain, Ltd.

(57) ABSTRACT

The invention relates to a *Cleome droserifolia* extract for topical application to the skin and/or mucous membranes. The invention also relates to the use of such an extract as well as to a process for obtaining it and to the compositions containing same.

11 Claims, 9 Drawing Sheets

CLEOME DROSERIFOLIA EXTRACT AND THERAPEUTIC OR COSMETIC USE THEREOF

CROSS REFERENCE TO RELATED APPLICATIONS

This application is the U.S. National phase application corresponding to PCT/EP2020/068070 which was assigned an international filing date of Jun. 26, 2020 and associated with publication WO 2020/260611 A1 and which claims priority to FR 1907051, filed on Jun. 27, 2019, the disclosures of which are expressly incorporated herein by reference.

TECHNICAL FIELD

The invention relates to an extract of *Cleome droserifolia* exhibiting a therapeutic or cosmetic effect intended for topical application to the skin and/or mucous membranes. The invention also relates to the use of such an extract as well as to a process for obtaining it and to the compositions containing same.

BACKGROUND

The skin constitutes the envelope of the human body, in continuity with the mucous membranes which cover the cavities of the body.

The skin and mucous membranes form a protective barrier against the external environment and perform many vital functions. They are regularly assaulted and may be the subject of various pathologies.

To deal with skin disorders, there are active principles and specific compositions aimed at treating a given skin pathology or a particular unsightly manifestation. Regarding therapeutic or dermatological products for topical application, a majority of them are synthetic products and are not of natural origin. As for cosmetics, there are products of natural origin, but these are not always effective.

SUMMARY

Thus, an objective of the invention is to provide a solution of natural origin which can be used effectively in topical application for the treatment of numerous pathological disorders on diseased skin and/or mucous membranes, but also for cosmetic effects on healthy skin.

To achieve this objective, the invention proposes to use an extract of *Cleome droserifolia*.

*Cleome droserifolia* is a natural plant present in large quantities in several countries of the Near and Middle East.

Now, surprisingly, extracts of *Cleome droserifolia*, and in particular:
extracts obtained with a solvent comprising at least water, namely:
aqueous extracts (solvent consisting exclusively of water) or
obtained using water-based solvent(s) (hydroalcoholic solvent or solvent consisting of a mixture of water and organic solvent), or
extracts obtained by supercritical $CO_2$ extraction,
exhibit powerful effects on many skin or mucous membrane pathologies, but also cosmetic effects when applied to healthy skin, in particular an antioxidant effect that can act as an anti-aging agent.

An extract of aerial parts of *Cleome droserifolia* obtained by hydrodistillation is already known, said extract having antioxidant properties. Such a process is described in particular in the article Ahmed M. Abd El-Gawad et al. 2018 and Riyadh Muhaidat et al. 2015. However, such an extraction process makes it possible to obtain essential oils and not an aqueous extract, and no therapeutic or cosmetic skin application is suggested or considered. The article Sharad M. et al. 1992 describes a process for the ethanolic (EtOH) extraction of aerial parts of *Cleome droserifolia*. Thus, said extract is not obtained with a solvent comprising at least water. Finally, the article Hegazy et al. 1995 teaches us a process for the aqueous extraction of aerial parts of *Cleome droserifolia*. However, cosmetic or therapeutic use in topical application of said extract obtained is not described.

The invention is therefore specifically aimed at an extract of *Cleome droserifolia* intended for topical application (for therapeutic or cosmetic purposes) to the skin and/or the mucous membranes, for the treatment of the skin and/or the mucous membranes, said extract preferably being an aqueous or hydroalcoholic extract, or being obtained using a solvent comprising water and an organic solvent or obtained by extraction with supercritical $CO_2$. Preferably, said extract is not obtained by hydrodistillation and is not an essential oil.

Advantageously, the extract according to the invention is obtained from a little-used plant, available at low cost over a large area extending over several countries, without requiring fertilizer, pesticide or any other chemical product. In addition, water is preferably the main solvent, or even the only solvent, used to obtain the extracts according to the invention, so that the extract according to the invention is included in green chemicals. This is also the case with supercritical $CO_2$ extraction. Furthermore, *Cleome droserifolia* is not toxic.

Another advantage of the active extract according to the invention is that the product is highly soluble in water so that it can be formulated in various formulations for topical application.

Another object of the invention is an extract of *Cleome droserifolia* for its use in topical application in the treatment of the skin and/or mucous membranes, in particular for an anti-coagulant and/or anti-bleeding and/or healing and/or antioxidant and/or anti-inflammatory and/or anti-itch and/or anti-bacterial and/or anti-histamine and/or anti-allergic effect. Another object of the invention is an extract of *Cleome droserifolia* for its use in topical application in the treatment of diseases of the skin and/or of the mucous membranes, in particular as a medication. The term disease also means pathology, aggression or condition.

The invention also relates to the cosmetic use of an extract of *Cleome droserifolia* on healthy skin for cosmetic applications, in particular anti-aging and/or anti-redness and/or for a repairing and/or moisturizing effect on healthy skin after UV exposure.

Another object of the invention consists of compositions comprising at least 0.1% by weight of an extract of *Cleome droserifolia*, as well as the therapeutic (in particular dermatological) or cosmetic uses of these compositions.

Finally, the invention relates to a specific process for obtaining an extract according to the invention, comprising at least the implementation of the following steps:
drying, then grinding of aerial parts of *Cleome droserifolia*,
extracting: aqueous extraction (with a solvent consisting exclusively of water) or use of a hydroalcoholic solvent or use of a solvent consisting of a mixture of water and organic solvent or extraction with supercritical $CO_2$, with a proportion of *Cleome droserifolia* between 5 and 20% and a proportion of solvent between 80 and 95%, the percentages being given by weight relative to the total weight of the mixture of the dried and ground aerial parts of *Cleome droserifolia* and solvent, filtering to remove particles in suspension, obtaining a liquid extract.

The invention is now described in detail, in particular with regard to non-limiting examples, test results and the appended figures below.

DETAILED DESCRIPTION OF THE INVENTION

Definitions

Figures 1A, 1B, 1C, 1D, 1E, 1F:
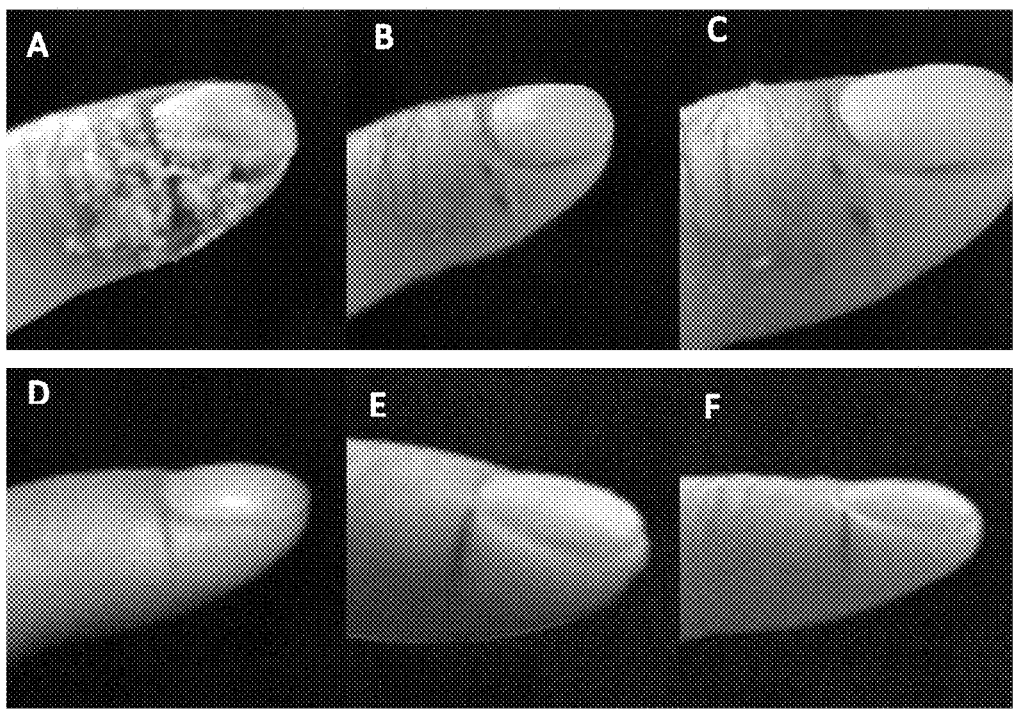
FIG. 1A is a photograph of a cut finger, taken on d0 at 11:36 a.m. to which a composition comprising an extract according to the invention has just been applied.
FIG. 1B is a photograph of a view from the same finger as FIG. 1*a* taken on d0 at 11:50 a.m.
FIG. 1C is a photograph of another view from the same finger as FIGS. 1*a* and 1*b*, taken on d0 at 11:50 a.m.
FIG. 1D is a photograph of a view from the same finger as FIGS. 1*a*, 1*b* and 1*c*, taken on d0 at 8:05 p.m.
FIG. 1E is a photograph of a view from the same finger as FIGS. 1*a*, 1*b*, 1*c* and 1*d*, taken on d+1 at 8:44 a.m.
FIG. 1F is a photograph of a view from the same finger as FIGS. 1*a*, 1*b*, 1*c*, 1*d* and 1*e*, also taken on d+1 at 8:44 a.m. from a different angle than in FIG. 1*d*.
Figures 2A, 2B, 2C, 2D, 2E:
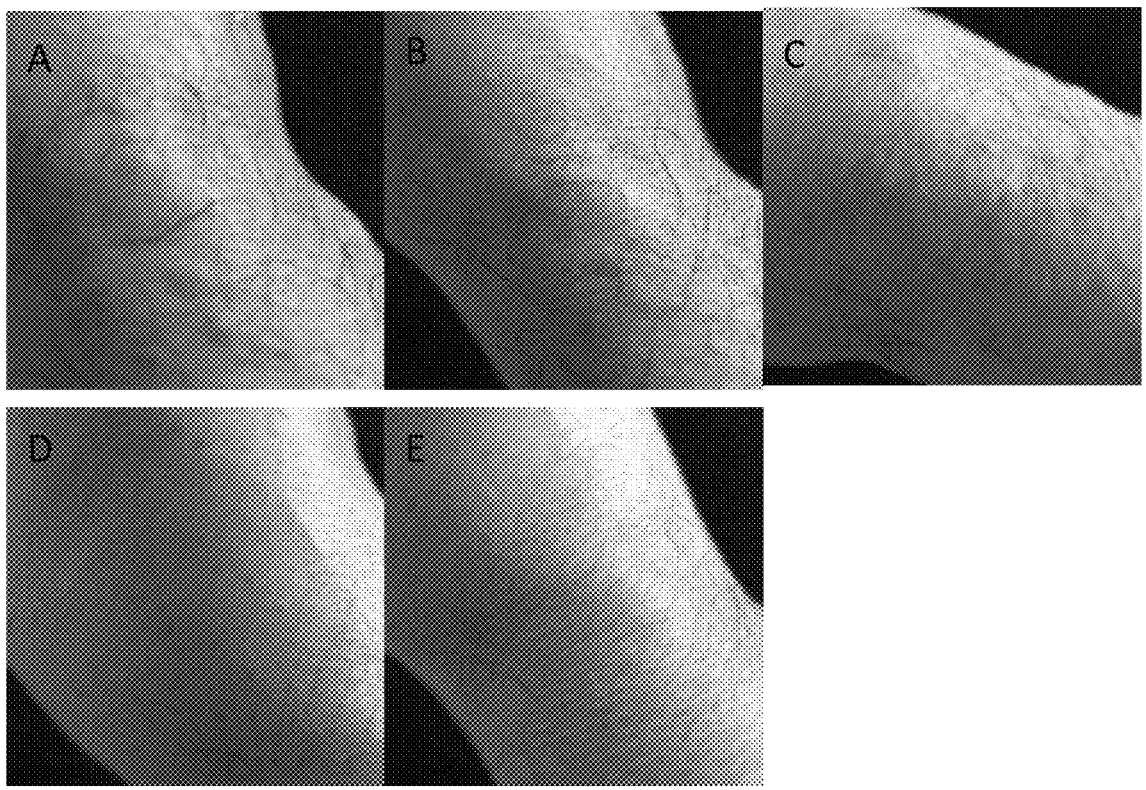
FIG. 2A is a photograph of a forearm showing hives, taken on d0 at 3:44 p.m. to which a composition comprising an extract according to the invention has just been applied.
FIG. 2B is a photograph of the same forearm as that of FIG. 2*a*, taken on d0 at 3:56 p.m.
FIG. 2C is a photograph of the same forearm as that of FIGS. 2*a* and 2*b*, taken on d0 at 4:11 p.m.
FIG. 2D is a photograph of the same forearm as that of FIGS. 2*a*, 2*b* and 2*c*, taken on d0 at 5:22 p.m.
FIG. 2E is a photograph of the same forearm as that of FIGS. 2*a*, 2*b*, 2*c* and 2*d*, taken on d0 at 7:13 p.m.

"Extract" of *Cleome droserifolia*, within the meaning of the invention, means at least one molecule, preferably a set of molecules obtained from *Cleome droserifolia*.

"Therapeutic effect" or "therapeutic use," within the meaning of the invention, means a curative or preventive effect or a use in treatment or prevention, to treat a pathology, a pathological state or a symptom of a pathological state or a symptom of a pathology. This may be a dermatological effect or use when applied to diseased skin.

"Aqueous extract," within the meaning of the invention, means an extract obtained from a solvent consisting exclusively of water.

"Hydroalcoholic extract," within the meaning of the invention, means an extract obtained from a solvent consisting of water and at least one alcohol.

"Healthy skin," within the meaning of the invention, means a skin which is not sick or which does not have pathological disorders, but which may possibly include non-pathological unsightly manifestations such as wrinkles, fine lines, dryness, pigmentation, redness etc.

*Cleome droserifolia* Extract

According to a first object, the invention relates to a particular extract of *Cleome droserifolia*, intended for topical application to the skin and/or the mucous membranes, said extract being an extract obtained with a solvent comprising at least water and/or obtained by supercritical $CO_2$ extraction. Preferably, it is an aqueous extract, hydroalcoholic or obtained using a solvent comprising water and an organic solvent. The extract according to the invention is not an essential oil.

Therefore, the extract according to the invention is obtained by an extraction carried out with one or more water-based solvent(s) consisting of:

water alone (aqueous extraction), or a mixture of water and alcohol (hydroalcoholic extraction), preferably a mixture consisting of 60 to 80% water and 20 to 40% alcohol by volume; the alcohol is preferably chosen from ethanol, methanol and isopropanol, preferably ethanol, or a mixture of water+organic solvent, preferably a mixture consisting of 60 to 80% water and 20 to 40% organic solvent by volume; the organic solvent is preferably chosen from triols such as glycerol, or esters such as ethyl acetate.

Advantageously, the use of such solvents has no negative impact on the environment and on human beings, and makes it possible to obtain extracts exhibiting very high efficiency in the curative or preventive treatment of healthy or diseased skin and/or mucous membranes. The extract according to the invention may also be obtained by extraction with supercritical $CO_2$. Supercritical fluid extraction is a process of extracting a solute from a substance using a supercritical fluid as an extraction solvent. This process can be compared to a liquid extraction process. Supercritical carbon dioxide ($CO_2$) is the most widely used fluid. Its advantages are above all its non-toxicity and its chemical inertness. During extraction, the conditions of use of supercritical carbon dioxide are above its critical points (critical temperature 31° C. and critical pressure 73 atm). Carbon dioxide goes into an intermediate state between the liquid state and the gaseous state, called the "supercritical" state. In this state, the $CO_2$ efficiently solubilizes certain categories of active ingredients. By restoring the initial pressure, the $CO_2$ returns to the gaseous state and releases the desired ingredients. The low operating temperatures preserve all of the active molecules. The supercritical $CO_2$ extraction may be used alone or in combination with a hydro-ethanolic extraction, accompanied by co-solvents such as ethanol or methanol, the action of which is complementary if certain desired active agents have a high polarity. This efficient extraction technique is respectful of the environment because the low operating temperatures preserve all of the active molecules.

The extract according to the invention may be in any form, in particular:
  in liquid form,
  in the form of a resinous gum soluble in water, or
  in the form of a lyophilisate (lyophilized powder), soluble, which can be dissolved in water.

These different forms allow different uses, in different types of compositions, depending on the intended uses. In addition, they allow optimum effectiveness of the active principle according to the invention and allow it to retain its initial properties.

Preferably, the extract of *Cleome droserifolia* according to the invention is an extract obtained from aerial parts of *Cleome droserifolia*, and in particular from leaves and/or bulbs containing the seeds.

The extract according to the invention may be obtained by any suitable process using a solvent comprising water and/or by extraction with supercritical $CO_2$. According to a particularly suitable embodiment, the extract according to the invention is obtained by a method comprising at least the implementation of the following steps:
  drying, then grounding aerial parts of *Cleome droserifolia*;
  aqueous extraction or using a hydroalcoholic solvent or using a solvent consisting of a mixture of water and organic solvent, with a proportion of *Cleome droserifolia* of between 5 and 20% and a proportion of solvent (water or mixture of water and alcohol or mixture of water and organic solvent) of between 80 and 95%, the percentages being given by weight relative to the total weight of the mixture of the dried and ground aerial parts of *Cleome droserifolia* and solvent,
  filtration to remove particles in suspension,
  obtaining a liquid extract.

The drying and grinding step may be carried out by any suitable method known to a person skilled in the art. If possible, it is preferable to separate the leaves from the bronchioles and subject them to fine grinding. The drying may be carried out according to the conventional methods of drying vegetable raw materials.

The grinding is preferably carried out with a particle size preferably less than 2 mm.

If the extraction is an aqueous extraction, it may be performed:
  by decoction at room temperature for 24 to 48 hours, or
  by infusion in water at a temperature between 40 and 60° C., then infusion and decantation for at least 24 hours at a temperature between 2 and 8° C., or
  by infusion in water at a temperature of at least 100° C. for 4 to 10 minutes, then infusion and settling, preferably for at least 24 hours at a temperature between 2 and 8° C.; this latter extraction method makes it possible to reduce the rate of microorganisms present in the extract obtained from the raw material.

The filtration step to remove the particles in suspension is preferably carried out with filtration between 1 and 1000 µm, in particular between 100 and 200 µm.

It may be performed on standard filter paper. The filter or the filter mesh (cloth adapted to the size of the filter) may be in particular made of polyethylene (PE), polypropylene (PP), polyamide/nylon (PA), polyester (PES), fluorinated polymer-type PTFE (Teflon), polyvinylidene fluoride (PVDF), E-CTFE or polyetheretherketone (PEEK).

Industrial filtration filter cloths and mesh may be made from many types of materials, synthetic materials as above, but also stainless steel. After the filtration step, the process may also include the following steps:
  possibly a storage step either between 2 and 8° C., or at a temperature below −20° C. until use,
  a sterilizing filtration step before use, for example a sterilizing vacuum filtration using a 0.2 µm filter. It may, in particular, be an ultrafiltration and/or a nanofiltration to possibly allow the retention of viruses.

The extract obtained is a liquid extract.

Thus, the invention also relates to an extract of aerial parts of *Cleome droserifolia* obtained by the extraction process as detailed above.

The method may comprise additional steps to obtain an extract in the form of a resin or an extract in the form of a lyophilisate, from this liquid extract. Thus, if the extract is in the form of a resinous gum, the process preferably also comprises a step of drying the liquid extract. This drying step may be carried out at a temperature between room temperature and 80° C.

Preferably, the liquid extract is subjected to hot air drying at a temperature between 45 and 80° C. The drying may be carried out, for example, in a closed chamber provided with a hot air discharge system.

After evaporation of the liquids contained in the extract, a blackish resinous gum is obtained. This resin or resinous gum is soluble in water.

If the extract is in the form of a lyophilisate, the method preferably also comprises a step of lyophilization of the liquid extract. Lyophilization may be carried out by implementing the following steps:
  freezing of the liquid extract at a temperature between −20° C. and −40° C. for 24 to 72 hours,
  lyophilization for 100 to 150 hours at a temperature between −20° C. and −80° C. and a pressure between 0.10 mbar and 0.40 mbar. The lyophilisate is preferably in the form of a cake of yellow powder in the form of needle crystals.

The lyophilized form of the active principle according to the invention is soluble in water. The apparent solubility is preferably greater than 43 mg/g. Thus, the extract according to the invention is preferably either in liquid form (before or after filtration), or in the form of a dry extract (resin or lyophilisate). The extract according to the invention may be used in a composition, but it may also be used as either in the form of a liquid extract, or in the form of a lyophilized powder or a resin.

Compositions Including an Extract of *Cleome droserifolia*

Therefore, the invention also relates to a composition comprising an extract of *Cleome droserifolia*, in particular a composition comprising at least 0.1% by weight of an extract according to the invention, preferably comprising between 0.1% and 5%.

The compositions according to the invention are suitable for topical application. It is either a medication, or a dermatological composition, or a cosmetic composition.

The compositions according to the invention comprise, in addition to the active principle obtained from *Cleome droserifolia*, a medium suitable for use on the skin and/or the mucous membranes.

Advantageously, the high solubility in water of the extracts of *Cleome droserifolia* according to the invention makes it possible to produce galenic formulations for combating infections of the mucous membranes such as the oral mucosa, the vaginal mucosa, the anal mucosa and the skin.

The compositions according to the invention may be provided in different galenic forms suitable for topical application to the skin and/or the mucous membranes. They may be, in particular, a cream, an ointment, a gel, a paste, a lotion, an unguent toothpaste, a soap, a mouthwash, a shampoo, a shaving cream, a patch or a bandage.

The compositions according to the invention also comprise a physiologically acceptable medium in addition to the active principle.

Uses of an Extract of *Cleome droserifolia* and Compositions Containing Same

The extracts of *Cleome droserifolia* and the compositions containing same exhibit remarkable properties when used, on the one hand, on healthy skin and/or mucous membranes to improve the aesthetic appearance of the skin and, on the other hand, on skin that presents a pathological disorder (burn, wound, rash, canker sores, etc.).

In particular, the extracts of *Cleome droserifolia*, and in particular the extracts according to the invention, exhibit:
- an antioxidant activity,
- a coagulant activity of the plasma,
- an anti-bleeding activity,
- a healing activity,
- an antibacterial activity, in particular inhibitory activity against rapidly growing *mycoplasma*,
- an anti-histamine activity
- an anti-itching activity,
- an anti-inflammatory activity,
- an anti-allergic activity.

Thus, the invention also relates to an extract of *Cleome droserifolia*, preferably an extract according to the invention, or a composition containing same, for its use in topical application for the treatment of the skin and/or of the mucous membranes, for the treatment of skin and/or mucous membrane pathologies and, in particular, for an anti-coagulant and/or anti-bleeding and/or healing and/or antioxidant and/or anti-inflammatory and/or anti-itching and/or anti-bacterial and/or anti-histamine and/or anti-allergic effect. According to a preferred embodiment, the extract of *Cleome droserifolia* for its use is not obtained by hydrodistillation and is not an essential oil.

The invention also relates to an extract of *Cleome droserifolia*, preferably an extract according to the invention, or a composition containing same, for its use in topical application for the treatment of skin and/or mucous membrane pathologies even more preferably inflammatory and/or allergic diseases and in the healing of the skin and/or mucous membranes, in particular as a medication.

According to one embodiment, the invention relates to an extract of *Cleome droserifolia* or a composition containing same, for its use for the treatment of pathologies with an inflammatory and/or atopic profile having a Th1 and/or Th17 and/or Th2 cytokine profile (Th1, Th17 and Th2 being helper T lymphocytes).

An extract of *Cleome droserifolia*, in particular an extract according to the invention or a composition containing same, may, in particular, be used:
- as an active ingredient or anti-inflammatory composition for the skin and mucous membranes, and/or
- as an active ingredient or soothing and/or anti-itching composition for the skin and mucous membranes, and/or
- as an active ingredient or healing and/or coagulant composition for cutaneous, oral, vaginal or anal use, and/or
- as an active ingredient or composition for skin hygiene and/or intimate hygiene (oral, vaginal, anal), in particular to prevent infections such as mycoplasmas, and/or
- as an active ingredient or anti-allergic composition.

Therefore, the extract of *Cleome droserifolia*, in particular the extract according to the invention, or the compositions containing same, may be used for a therapeutic effect in the treatment of various pathological skin disorders and, in particular, in the treatment of urticaria, infections of the skin and/or mucous membranes, fungal infections of the skin and/or mucous membranes, atopic dermatitis, psoriasis, acne, rosacea, herpes, canker sores, burns, insect bites, burns, especially burns from sunburn, rashes and/or sores.

Furthermore, on healthy skin, the extract according to the invention exhibits an effect which improves the aesthetic appearance of the skin. In particular, its antioxidant effect allows use for many cosmetic applications and, in particular, for anti-redness effects and/or anti-aging effects, that is to say, for preventing or combating the appearance of unsightly signs due to skin aging, such as wrinkles, fine lines, skin dryness, etc.

Therefore, the invention relates to the cosmetic use of an extract of *Cleome droserifolia* according to the invention, or of a composition containing such extract, on healthy skin, in topical applications, in particular for an anti-aging cosmetic effect and/or to reduce redness (anti-redness effect) of the skin caused by exposure to the sun or UV rays.

According to a particular aspect of the invention, an extract of *Cleome droserifolia*, and in particular an extract according to the invention, exhibits a biostimulating activity on the growth of human keratinocytes, an improvement in the healing of sores and thus makes it possible to regenerate human skin. The extract of *Cleome droserifolia*, and in particular the extract according to the invention, may thus be incorporated into compositions for aftershave, creams for healing the skin or mucous membranes, or else formulated in plasters or adjuvants for skin ulcers or bedsores.

Likewise, an extract of *Cleome droserifolia*, and in particular an extract according to the invention, is capable of stimulating the synthesis and excretion of collagen in the extracellular matrix. The extract can thus be used in compositions, in particular in ad hoc galenic formulations, to stimulate the synthesis and excretion of collagen and to fight against aging of the skin as well as scarring of the skin.

In addition, an extract of *Cleome droserifolia*, and in particular an extract according to the invention, exhibits an inhibitory effect on the secretion of IL-6, on the secretion of IL-8 and on the secretion of MDC. The treatment of skin cells with an extract of *Cleome droserifolia*, and in particular an extract according to the invention, also makes it possible to restore the expression of filaggrin depressed by TNF-α/IFN-γ.

Thus, an extract of *Cleome droserifolia*, and in particular an extract according to the invention, can be used as an anti-inflammatory and anti-allergic product, but also as a product for moisturizing the skin and as a barrier function.

In order to illustrate the effects on the skin and the mucous membranes of active ingredients comprising extracts obtained from *Cleome droserifolia*, examples and test results are presented below.

EXAMPLES

Example 1: Example of Active Principle According to the Invention in Liquid Form (Aqueous Extract)

The aerial part of *Cleome droserifolia* is collected and dried. The leaves are separated from the bronchioles to be subjected to fine grinding.

An aqueous extract is produced. The extraction is carried out for 36 hours in water at room temperature.

The proportion of dried and ground raw materials is 10% for 90% weight/weight of water. A brown-colored infusion with aromatic flavors is obtained.

The decoction is then subjected to filtration through a standard filter paper in order to remove the particles in suspension.

The aqueous extract is stored either in the refrigerator at 2-8° C. or in the freezer at −20° C. until use. Before use, the aqueous extract is subjected to sterilizing filtration under vacuum using a 0.2 μm filter of the Nalgen type. The liquid extract obtained is soluble in water.

Example 2: Example of Active Principle According to the Invention in Liquid Form (Aqueous Extract)

The aerial part of *Cleome droserifolia* is collected and dried, then finely ground.

An aqueous extract is produced. The extraction is carried out by infusion in hot water heated from 40° C. to 60° C., followed by infusion and decantation for 24 hours in the refrigerator at 4° C.

The proportion of dried and ground raw materials is 12% for 88% water weight/weight. A brown-colored infusion with aromatic flavors is obtained.

The decoction is then subjected to filtration through a standard filter paper in order to remove the particles in suspension.

The aqueous extract is stored either in the refrigerator at 2-8° C. or in the freezer at −20° C. until use. Before use, the aqueous extract is subjected to sterilizing filtration under vacuum using a 0.2 μm filter.

The liquid extract obtained is soluble in water.

Example 3: Example of Active Principle According to the Invention in Liquid Form (Aqueous Extract)

The aerial part of *Cleome droserifolia* is collected and dried, then finely ground.

An aqueous extract is produced. The extraction is carried out as follows: the leaves of *Cleome droserifolia* dried and ground in boiling water (100° C.) are added and left to boil for 5 minutes to extract the water-soluble compounds. They are then left to infuse and decant in the refrigerator for 24 hours at 2 to 8° C.

The proportion of dried and ground raw materials is 9% for 91% water weight/weight. A brown-colored infusion with aromatic flavors is obtained.

The decoction is then subjected to filtration through a standard filter paper in order to remove the particles in suspension.

The aqueous extract is stored either in the refrigerator at 2 to 8° C. or in the freezer at −20° C. until use. Before use, the aqueous extract is subjected to sterilizing filtration under vacuum using a 0.2 μm filter of the Nalgen type.

The liquid extract obtained is soluble in water.

Example 4: Example of Active Principle According to the Invention in Liquid Form (Hydroalcoholic Extract)

The aerial part of *Cleome droserifolia* is collected and dried, then finely ground.

A hydroalcoholic extract is produced. The extraction is carried out as follows: the leaves of *Cleome droserifolia*, dried and ground in a boiling hydroalcoholic mixture (70% water—30% ethanol), are added and left to boil for 5 minutes to extract the compounds soluble in the water. They are then left to infuse and decant in the refrigerator for 24 hours at 2-8° C. The proportion of dried and ground raw materials is 10% for 90% weight/weight of hydroalcoholic mixture. A brown-colored infusion with aromatic flavors is obtained.

The decoction is then subjected to filtration through a standard filter paper in order to remove the particles in suspension.

The hydroalcoholic extract is stored either in the refrigerator at 2 to 8° C., or in the freezer at −20° C. until use. Before use, the extract is subjected to sterilizing filtration under vacuum using a 0.2 μm filter of the Nalgen type. The liquid extract obtained is soluble in water.

The liquid extract obtained is soluble in water or in hydroalcoholic solution.

Example 5: Example of Active Principle According to the Invention in Resin Form

The liquid extract of Examples 1 to 3 is subjected to drying in hot air at 60° C. in a closed chamber provided with a system for discharging the hot air pulsed by dryers.

After evaporation, a blackish resinous gum is obtained.

The resinous gum obtained is soluble in water.

Example 6: Example of Active Principle According to the Invention in the Form of Lyophilisate A LIOBRAS brand model L101 laboratory freeze dryer with a capacity of 3.0 liters of ice per 24 hour cycle and a total capacity of 5.0 liters was used at a working temperature of −55° C.

The liquid extract from Examples 1 to 3 was frozen at −30° C. for 48 hours.

It was then lyophilized for 120 hours at an internal temperature and pressure of −45° C. and 200 μmHg, respectively.

Figure 3:
FIG. 3 is a photograph of a lyophilisate obtained by lyophilization of a liquid extract according to the invention.

At the end of the lyophilization cycle, a cake of yellowish powder in the form of needle crystals is obtained as shown in FIG. 3.

The lyophilized form is soluble in water.

Example 7: Example of Composition in the Form of a Gel

An example of a composition in gel form is presented below.

In this example, the composition consists of:

| | |
|---|---|
| Hydroxyethylcellulose | 1.8% |
| Propylene glycol | 0.5% |
| Imidazolidinylurea | 5 drops (5% sol. In propylene glycol) |
| *Cleome droserifolia* | between 0.1 and 5%, preferably between |

-continued

| | |
|---|---|
| (Example 6) | 0.12 and 2% |
| Distilled water | q.s.p. 100.0% |

This composition may be obtained according to the procedure described as follows:
- dissolve the extract of *Cleome droserifolia* in distilled water by heating to 40° C. while stirring
- add the necessary quantity of hydroxyethylcellulose and maintain stirring until a gel is obtained
- leave to cool while maintaining stirring, then add the propylene glycol and the imidazolidinylurea.

Example 8: Example of Composition

An example of a composition in the form of a nonionic cream is presented below. In this example the composition consists of:

| | |
|---|---|
| Polawax ™ NF | 9.0% |
| Cetyl alcohol | 5.0% |
| Cetiol ® V | 4.0% |
| Propylene glycol | 4.0% |
| Imidazolidinylurea | 3 drops (5% sol. In propylene glycol) |
| *Cleome droserifolia* (example 6) | between 0.1 and 5%, preferably between 0.12 and 2% |
| Distilled water | q.s.p 100.0% |

This composition may be obtained according to the procedure described as follows:
- in a bowl, add the Polawax, cetyl alcohol and Cetiol V and heat on a hot plate at a temperature of 75° C.
- in a beaker, add the distilled water and propylene glycol at a temperature of 70° C.,
- then slowly pour the aqueous phase into the oily phase while stirring
- remove from the heating system and stir slowly until cool.
- at 50° C., add the imidazolidinylurea solution, then add the extract of *Cleome droserifolia* previously dissolved in water.

Example 9: Example of Composition in the Form of a Soap

An example of a composition in the form of a soap is presented below.
In this example, the composition consists of (for a mixture of 625 g):

| | |
|---|---|
| Olive oil: | 330.0 g (52.80%) |
| Bay laurel oil: | 84.0 g (13.44%) |
| H$_2$O: | 134.4 g (21.51%) |
| KOH or NaOH: | 51.6 g (8.26%) |
| *Cleome droserifolia* (Example 6) | 25.0 g (between 0.5 and 4%) |

The liquid extract from one of Examples 1 to 4 may also be used. In this case, the dry extract must represent 25% by mass of the extract.
The operating protocol is described as follows:
- Weigh the oils
- Weigh the water
- Weigh the extract of *Cleome droserifolia* lyophilized or in resin form
- Weigh the NaoH or the KOH
- Dissolve the KOH or the NaOH in water and wait for the temperature to drop to 60°-80° C.
- Add the extract of *Cleome droserifolia* and stir the whole until the compounds have completely dissolved.
- Pour the solution thus prepared into a receptacle containing the previously homogenized oils.
- Stir with the propeller stirrer until a trace is obtained.
- Pour into molds and let stand 24 to 48 hours
- Unmold and let the soap cure for 4 weeks to 9 months before use Variants may be prepared by adjusting the total oil content as well as the nature of the oils. The total oil value may vary between 70 and 80%.
Amounts of aromatic essential oils may be added such as essential oil of rosemary, cypress, peppermint, Ylang-Ylang, patchouli, etc.
The *Cleome droserifolia* extract content for this example may vary between 0.1% and 5%.

Example 10: Comparison of the Extraction Yields of Different Processes for Obtaining *Cleome droserifolia* Extract Solvent=Water 180 ml of demineralized water are brought to reflux in a container. 20 g of aerial parts of *Cleome droserifolia* are then added, then the mixture is left under stirring for 5 min at reflux. The heating is turned off and the mixture is left under stirring for 12 h. Allowed to settle, then filtered under vacuum (porosity 3). The filtrate is concentrated under vacuum at 40-50° C. An ocher solid with a mass of 7.6 g is obtained (store at −20° C.). The extraction yield obtained is 38%.

Solvent=Alcohol 180 ml of absolute ethanol are brought to reflux in a container. 20 g of aerial parts of *Cleome droserifolia* are then added, followed by stirring for 50 min at reflux. The heating is turned off and the mixture is left under stirring for 18 h. Allowed to settle, then filtered under vacuum (porosity 3). The filtrate is concentrated under vacuum at 40-50° C.

A green resin with a mass of 4.67 g is obtained (store at −20° C.). The extraction yield obtained is 23%.

Solvent=Water+Alcohol 180 ml of an absolute ethanol/demineralized water (50/50) mixture are brought to reflux in a container. 20 g of aerial parts of *Cleome droserifolia* are then added, then the mixture is left for 60 min under stirring at reflux.

The heating is turned off and the mixture is left stirring for 16 h. Allowed to settle, then filtered under vacuum (porosity 3). The filtrate is concentrated under vacuum at 40-50° C.

A brown solid is obtained with a mass of 6.9 g (store at −20° C.). The extraction yield obtained is 34%.

Thus, the extraction yields are better when the solvent comprises water. All the examples may be adapted to be carried out at larger production scales.

Evaluation of the Effect of an Extract or Composition Containing the Extract According to the Invention Evaluation of the effect on the activity on blood coagulation and healing of an extract according to the invention:

The aim of this test is to evaluate the activity of the extract of *Cleome droserifolia* according to the invention (extract of the example dissolved in water at a concentration of 2 mg/ml) on coagulation and to observe the effect thereof compared to the reference standard of unfractionated heparin, using the model of in vitro based on the determination of the response by measuring the coagulation time.

Two methods in vitro and in humans were used:

Coagulant Activity In Vitro:

The material used is described as follows:

The 6th international standard for unfractionated heparin (WHO 07; 328)

Activated cephaloplastin reagent Dade® Actin®—Siemens

Calcium chloride—Siemens®.

Thermo Scientific coagulometer

Citrated ovine plasma 8.7%.

Aqueous extract of lyophilized *Cleome droserifolia*

The operating protocol is described as follows:

The lyophilized extract was dissolved in ultrapure water to obtain a stock concentration of 2 mg/ml. Dilution was carried out to obtain a concentration of 0.6 mg/ml.

In a first experiment, 100 μl of each of the following solutions was added to the cuvettes of the coagulometer (n=2):

Lyophilisate solution concentrated at 0.6 mg/ml,
Heparin solution at a concentration of 0.6 IU/ml
Physiological solution for the control group, Then, 100 μl of sheep plasma was added to all the wells.

After 2 minutes, 100 μl of reactant activated with Cephalosplatin Cade® Actin was added.

After 5 minutes of incubation, 100 μl of calcium chloride solution were added and the coagulation times were recorded.

The invention (lyophilisate of *Cleome droserifolia* (Example 7) diluted to 0.6 mg/ml) gave mean coagulation times of 30.3 seconds, while the control group showed a coagulation time of 32.4 seconds.

In a second experiment, the solution of *Cleome droserifolia* at a concentration of 2 mg/ml reduced the coagulation times to 14.6 seconds, while the control showed a coagulation time of 32.2 seconds. The tests were compared to heparin, which showed coagulation times of 54.3 seconds at a concentration of 0.6 IU/ml.

A summary of the results obtained is presented in Table 1.

TABLE 1

| Coagulating activity | | |
| --- | --- | --- |
|  | Concentration | Coagulation time |
| Physiological solution | 0.9% NaCl | 32.4 |
| Invention (Example 6) | 2.0 mg/ml | 14.6 |
| Heparin | 54.3 U/ml | 54.3 |

Therefore, the data obtained demonstrate the pro-coagulant activity of an extract of *Cleome droserifolia* according to the invention, by a significant reduction in the coagulation time of the ovine plasma used as substrate by comparison with the control.

Coagulant and Healing Activity in Humans of an Extract According to the Invention:

The coagulating and healing effect described below was confirmed in an experiment in humans.

To carry out this experiment, a small amount of dry extract of *Cleome droserifolia* in lyophilized form was deposited on wounds.

An example is given below and shown in FIGS. 1a, 1b, 1e, 1d, 1e and 1f, for an incision of the left index finger of a person with drip bleeding, caused by improper handling of a kitchen knife.

Fourteen minutes after the extract was deposited on the wound, the latter was rinsed with a gauze soaked in mineral water. The evolution of the wound was monitored over time, and photographs taken.

It is observed that after depositing the lyophilisate, the bleeding stops immediately (FIG. 1a).

After rinsing after 14 minutes post application, the wound exhibits a very neat, clean, non-bleeding skin incision and skin suggesting onset of healing. (FIGS. 1b and 1c).

The finger was re-examined for 9 hours 30 minutes after application of the product. The wound was well healed with a coagulated crust of blood. (FIG. 1d).

The same observations were made the next day, i.e., after 21 hours and 8 minutes post application (FIGS. 1e and 1f).

No other product was used in parallel.

This result confirms the coagulating and healing effect of an extract of *Cleome droserifolia* according to the invention demonstrated in vitro.

Evaluation of the Antioxidant Effect of an Extract According to the Invention:

The objective of this study is to determine the antioxidant activity of an extract of *Cleome droserifolia* according to the invention (extract of the example dissolved in water at a concentration of 2 mg/ml) using the NCTC clone 929 cell line, after oxidative stress induced by hydrogen peroxide to determine cell viability.

The material used is described as follows:

Hydrogen peroxide

Ascorbic acid as a positive antioxidant control

NCTC 929 clone cell line (ATCC number CCL-1)

MEM culture medium, from Sigma-Aldrich®

MTT coloring

PBS solution, Sigma-Aldrisch®

Stock solution concentrated at 2 mg/ml of a lyophilisate of aqueous extract of *Cleome droserifolia* at 10%.

The operating protocol is described as follows:

In a 96-well plate, place the cells at a concentration of $3.5 \times 10^5$ cells/ml.

Incubate for 24 hours in an incubator set to 5% $CO_2$ and 37° C.

Remove the supernatant after 24 hours of incubation

In each well, deposit respectively 200 μl of the stock solution of lyophilisate diluted in MEM medium to ⅓ and ⅙ (i.e., 0.67 mg/ml and 0.33 mg/ml of lyophilized extract respectively), 200 ml of ascorbic acid at 0.56 mg/ml in MEM medium as positive control and 200 μl of MEM culture medium as negative control.

Incubate again for 24 hours, then add 100 μl of hydrogen peroxide at 25 μM diluted in sterile and pyrogen-free water.

Leave to incubate for 3 additional hours, then wash with PBS and add 20 μl of an MTT dye solution at a concentration of 5 mg/ml in the MEM medium Incubate for 2 additional hours then add to each well 100 μl of SDS at a concentration of 24% and shake the plate using the plate shaker for 10 minutes Carry out the optical density reading on the plate reader at the wavelength of 570 nm.

The method for calculating antioxidant activity (AO) is calculated as follows: AO=Mean absorbance obtained by the sample×100/Mean absorbance obtained by the negative control with MEM medium.

The cell viability results presented in Table 2 show a powerful capacity of ascorbic acid at 0.56 mg/ml and of the extract according to the invention at the concentrations of 0.67 mg/ml and 0.33 mg/ml to prevent the oxidative effect induced by hydrogen peroxide at 25 μM on cells of the NCTC line.

The extract of *Cleome droserifolia* according to the invention demonstrates an antioxidative capacity comparable to that of ascorbic acid.

TABLE 2

Evaluation of the antioxidant activity of aqueous extract of *Cleome Droserifolia* lyophilized on a cell line NCTC (3.5 × 105 cells/ml)

| Absorbance | Negative control MEM medium | Without $H_2O_2$ | | | | With $H_2O_2$ (25 µM) | | |
|---|---|---|---|---|---|---|---|---|
| | | Lyophilisate 0.67 mg/ml | Lyophilisate 0.33 mg/ml | Positive control ascorbic acid 0.56 mg/ml | $H_2O_2$ 25 µM | Lyophilisate 0.67 mg/ml | Lyophilisate 0.33 mg/ml | Positive control ascorbic acid 0.56 mg/ml |
| Mean | 0.4791 | 0.3049 | 0.4291 | 0.3719 | 0.0429 | 0.2833 | 0.3933 | 0.3564 |
| Std. deviation | 0.0078 | 0.0206 | 0.0321 | 0.0253 | 0.0027 | 0.0169 | 0.0276 | 0.0130 |
| CV (%) | 1.6340 | 6.7632 | 7.4917 | 6.7924 | 6.3130 | 5.9792 | 7.0252 | 3.6375 |
| Cellular viability (%) | | 63.64 | 89.56 | 77.61 | 8.95 | 59.13 | 82.09 | 74.38 |

These results show that the extract of *Cleome droserifolia* exhibits antioxidant and protective activity in relation to the oxidative effects induced by hydrogen peroxide. The ⅙ dilution shows results similar to those observed with ascorbic acid as a positive control.

Evaluation of the Anti-Inflammatory/Anti-Itching Effect of an Extract According to the Invention This study was performed in the clinical context described below.

A urticaria-type rash was visible on the wrist of a subject with symptoms characteristic of an itchy urticaria, an inflammation of the skin with localized vesicles.

The operating protocol for the study is described as follows:

After visualization, a liquid extract of *Cleome droserifolia* according to the invention (extract of the example dissolved in water at a concentration of 2 mg/ml) was applied to the inflammatory skin area using a cotton ball.

Observations were made as a function of time, post application. The application of the aqueous extract was carried out 10 minutes after observation. Then, observations were made as a function of time, photographs of the inflammatory zone were taken and the subject was questioned.

The results are shown in FIGS. 2a, 2b, 2c, 2d and 2e. Almost instantaneously after application of the *Cleome droserifolia* solution, the subject no longer presented any skin rash. Signs of reduced inflammation (redness and blisters) were visible to the naked eye within 3 minutes post application. The anti-inflammatory phenomenon continued over time as shown in the photos included in the figures.

These results show that an extract according to the invention significantly and very rapidly reduces the itching and inflammatory skin symptoms.

Evaluation of the Effect of an Extract According to the Invention on Rapidly Growing Strains of Mycobacteria The objective of this study is to evaluate the in vitro activity of an extract of *Cleome droserifolia* according to the invention (extract of the example dissolved in water at a concentration of 2 mg/ml) on the growth of rapidly growing mycobacteria (RGM) belonging to the group of non-tuberculous mycobacteria (NTM) by the micro-dilution technique.

The material used is described as follows:
Standard strains of RGM: *M. fortuitum* (ATCC 6841), *M. massiliense* (ATCC 48898) and *M. abscessus* (ATCC 19977)
Mueller Hinton (Himedia®) Agar Löwenstein-Jensen medium (HiMedia Pvt. Ltd Laboratories, India)
Dimethylsulfoxide (VETEC®)
TTC revealing dye
Mueller Hinton medium ((Himedia®)

The operating protocol is described as follows:
The sensitivity test was carried out according to the micro-dilution method in broth and according to the CLSI M07-A08 (CLSI, 2009).

The lyophilized extract was solubilized in dimethyl sulfoxide for the stock solution, for the preparation of working solutions which were diluted in Mueller Hinton broth. In 96-well plates, different concentrations of the extract were used from serial dilutions ranging from 1775 µg/ml to 27.73 µg/ml.

Then, the bacterial suspension of each of the bacteria studied was prepared from colonies maintained on Lowenstein-Jensen agar. A final inoculum of 5×105 CFU/ml was obtained from a standard McFarland scale inoculum of 0.5.

The inoculum was transferred to sterile microplates already added to the extract. The final volume of each well was 200 µL (100 µL of inoculum+100 µL of extract).

Reading of the plates, for determination of the minimum inhibitory concentration (MIC), was performed after incubation at 37° C. for 72 hours.

To reveal the growth or not of colonies of microorganisms, the test (2,3,5-triphenyltetrazolium chloride) at 1% was used.

The results obtained are presented in Table 3 below.

TABLE 3

| Rapidly growing mycobacteria (RGM) | Minimum inhibitory concentration (MIC in µg/ml) |
|---|---|
| *M. Abscessus* | 443.75 |
| *M. Massiliense* | 443.75 |
| *M. Fortiutum* | 443.75 |

It is observed that the extract of *Cleome droserifolia* according to the invention is capable of inhibiting the growth of mycobacteria of the rapid growth type at inhibitory concentrations equal to 443.75 µg/ml.

Evaluation of the Effect on Healing of an Extract According to the Invention:

The objective of this study is to evaluate the in vitro activity of an extract of *Cleome droserifolia* (dry aqueous extract of *Cleome droserifolia* in lyophilized form according to the invention) on skin healing, evaluated by re-epithelialization of artificial wounds through the migration of human HaCat keratinocytes.

The test is based on the measurement of the capacity of human HaCaT keratinocytes, cultured in the absence and in the presence of an extract of *Cleome droserifolia*, to close an artificial wound produced by scratching ("Scratch technique"). The capacity of the preparation to close the wound was compared to the control (DMEM culture medium containing 1% of fetal calf serum) and to the positive control in which 100 ng/ml of HB-EGF (Heparin-Binding EGF-like Growth Factor) were added. The extract according to the invention was used at 0.3 mg/ml, 0.75 mg/ml and 1.5 mg/ml in the culture medium. The healing follow-up took place over 2 days by image analysis at zero hour post-scratch, at 8 hours, at 24 hours, at 32 hours and at 48 hours.

For each condition, 3 culture wells were used. Each culture well was its own control relative to the wound surface observed at the initial time, immediately after scratching. The results were expressed as the mean of the percentage of healing compared to the initial time plus or minus the standard deviation. A Student test was performed to assess statistical significance.

Figure 4:
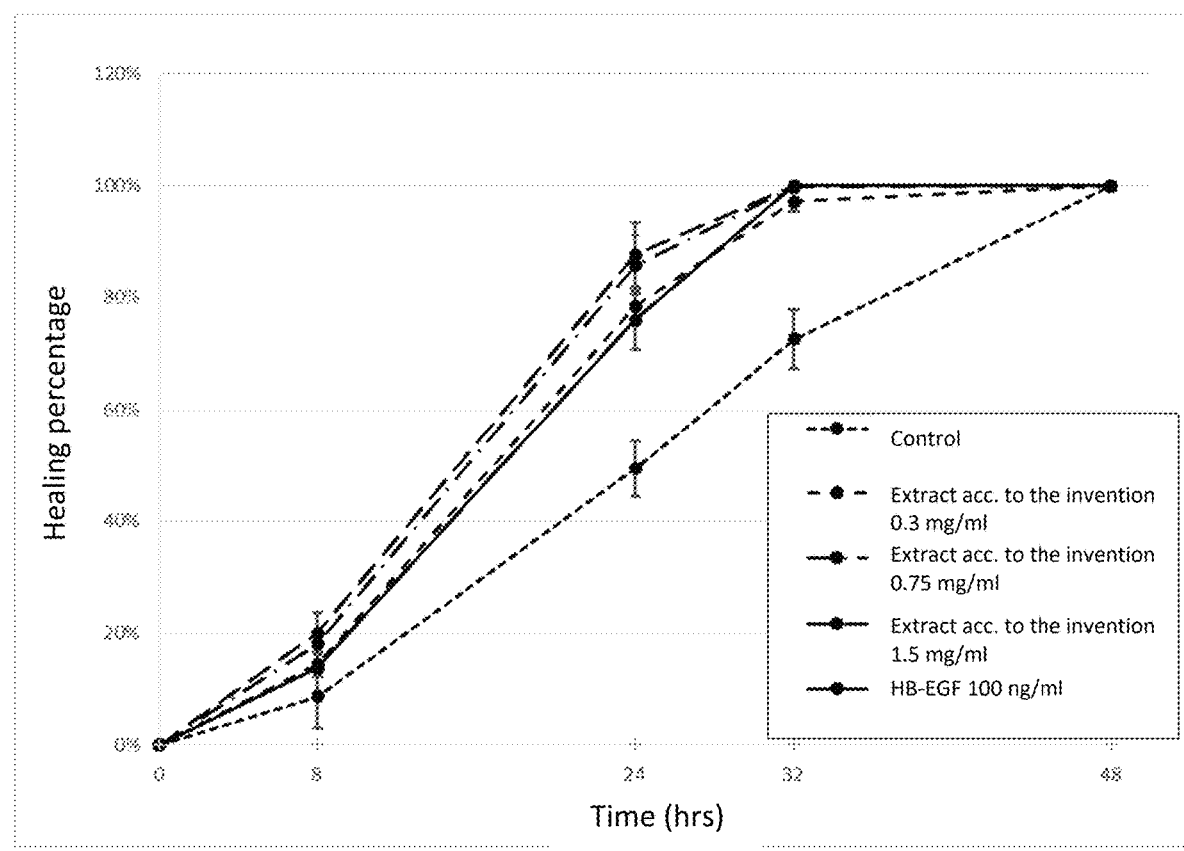
FIG. 4 represents skin healing by evaluation of the re-epithelialization of artificial wounds by migration of human HaCat keratinocytes.

The results are presented in FIG. 4. They show that the control wells exhibit a progressive reduction in the surface of the wounds with complete closure of the wounds at T4 (48 h), which shows an obvious stimulation of the wound healing kinetics at the cultures treated with extracts of Cleome droserifolia. In addition, the closure of the wounds of the wells at 1.5 mg/ml of the extract of Cleome droserifolia shows faster healing than that of the positive control (HB-EGF, 100 ng/ml).

These results show that the extract according to the invention exhibits a biostimulating activity on the growth of human keratinocytes, an improvement in the healing of wounds and thus makes it possible to regenerate human skin.

Evaluation of the Effect of an Extract According to the Invention on the Production of Extracellular Collagen:

The objective of this test is to evaluate the modulating effects of an extract of Cleome droserifolia (dry aqueous extract of Cleome droserifolia in lyophilized form according to the invention) on the synthesis of the extracellular matrix of the dermis. The test method is based on the production and deposition of the collagen matrix by human fibroblasts [NHDF] cultured in the absence or presence of the extract of Cleome droserifolia.

The test was carried out on NHDF dermal fibroblasts (strain F04.2H12), cultured in complete DMEM medium supplemented with ascorbic acid 2-phosphate (AA2P). Collagen levels were measured in dermal fibrillary matrices (ECMs) of cultures after treatment of cells for 14 days. The extract of Cleome droserifolia was tested at 3 non-cytotoxic concentrations: C1=0.2 mg/ml, C2=0.5 mg/ml and C3=1 mg/ml. The test solutions C1, C2 and C3 of the extract of Cleome droserifolia were prepared by successive dilution in DMEM culture medium containing 10% fetal calf serum and 0.1 mM L-ascorbic acid 2-phosphate (AA2P). The culture medium containing AA2P constituted the control group.

The total protein level of the extracts of the extracellular matrices obtained during the collagen extraction protocol was measured with the BCA Protein Assay kit (PIERCE™). At the same time, the collagen was quantified in the extracellular matrix using a SIRCOL calorimetric test (SIRCOL™ COLLAGEN ASSAY, BIOCOLOR®). The mean of the collagen levels (µg/ECM) was calculated in each experimental group, as were the means and standard deviations. The final results (Matrix Collagen, COLLMEC) are expressed in ng of collagen per µg of protein (µg/ECM).

Figure 5:
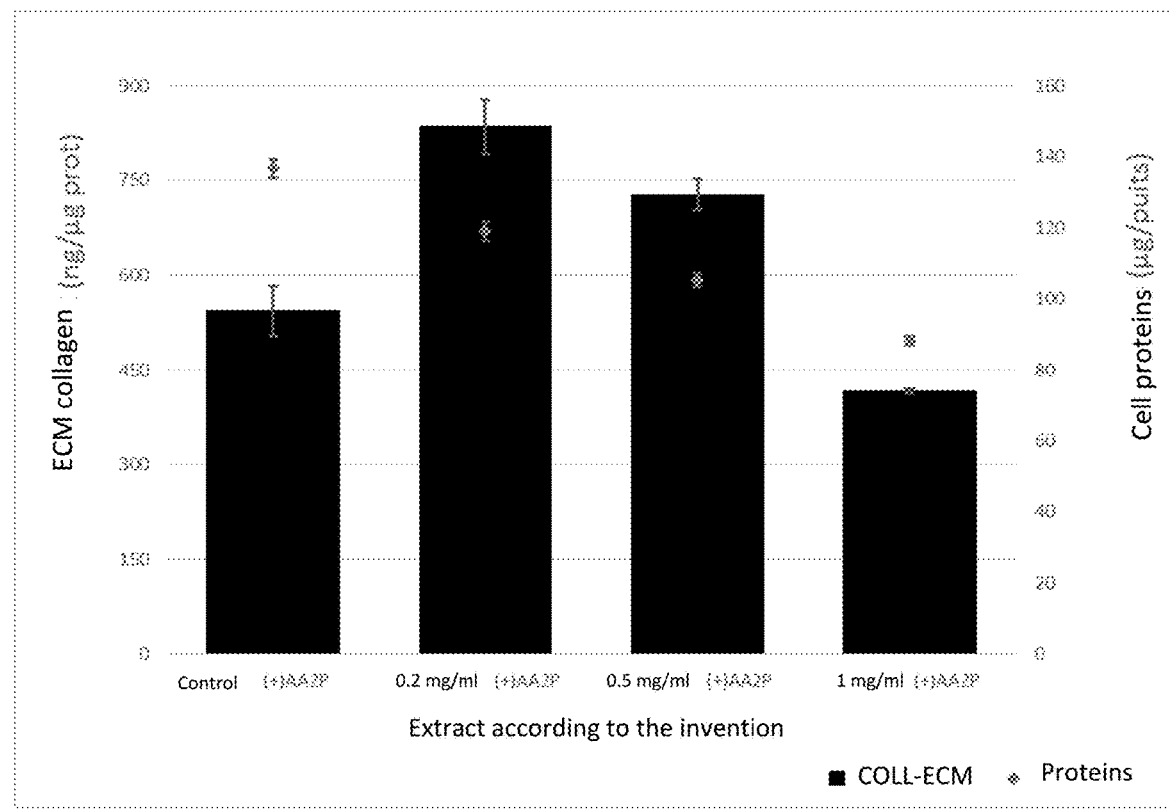
FIG. 5 shows the in vitro modulatory effects of the composition comprising the aqueous extract according to the invention on the synthesis of the extracellular matrix of the dermis.

In comparison with the control wells, the results, presented in FIG. 5, show that the extracellular matrix proteins decrease with the concentration of the product. At concentrations less than or equal to 0.5 mg/ml, the collagen level was strongly and very significantly increased with +53% for the 0.2 mg/ml concentration and +34% for the 0.5 mg/ml concentration ($p \leq 0.01$, Student's t-test). Conversely, at a concentration of 1 mg/ml, the collagen level was reduced by 23%.

Thus, these results demonstrate that the extract of Cleome droserifolia stimulates the synthesis and excretion of collagen in the extracellular matrix.

Evaluation of the Anti-Allergic Effect of an Extract According to the Invention by Measuring the Release of Histamine and C4 Leukotriene:

The modulating effect of the secretion of inflammatory intermediates was studied in vitro with an extract of Cleome droserifolia (dry aqueous extract of Cleome droserifolia in lyophilized form according to the invention) using MC/9 murine mast cells. The test was carried out on MC/9 in MC medium (DMEM high glucose+T-STIM+SVF (10%)+β-mercaptoethanol) in the absence (control) or presence (treated) of the test element, with (+) or without (−) exposure to PMA/A23187. The levels of mediators of allergy (histamine) and of inflammation (LTC4) were measured in the culture media, 24 hours after induction of the inflammatory stress by PMA (50 nM)/A23187 (1 µM). MC/9 cells were treated with Cleome droserifolia extract 24 hours before and 24 hours after PMA/A23187 stress. The concentrations of the preparation were used at the following concentrations: C1=70 µg/ml, C2=175 µg/ml and C3=350 µg/ml. Zileuton (Zileu) and Triprolidine (Triprol) were tested respectively at 300 nM and 30 µM, in parallel as positive control. Each test condition was performed in triplicate in 48-well plates.

The amount of histamine produced was measured in the culture incubation media after stimulation with PMA/A23187. The histamine was quantified by the Elisa technique with a "Histamine Elisa kit" assay kit (ENZO Life Sciences) by measuring the absorbance at 450 nm. The mean absorbances were calculated. The percentage of binding (B/B0%) was then calculated according to the instructions of the assay kit supplier. The histamine concentration of the samples was determined from the equation of the regression line of the calibration range.

The amount of LTC4 produced was measured in the culture incubation media after stimulation with PMA/A23187. LTC4 was quantified by the Elisa technique with a "CYSTEINYL LEUKOTRIENE Elisa kit" assay kit (ENZO Life Sciences) by measuring the absorbance at 405 nm. The mean of the absorbances of the replicates (n=3), corrected by subtraction from that of NSB, was calculated. The percentage of binding (B/B0%) was then calculated according to the instructions of the assay kit supplier. The histamine concentration of the samples was determined from the equation of the regression line of the calibration range. The crude levels of histamine (ng/ml) and LTC4 (pg/ml) deduced by interpolation from the standard curves were compared to the level of cellular proteins (µg/ml) of the corresponding wells.

Figure 6A:
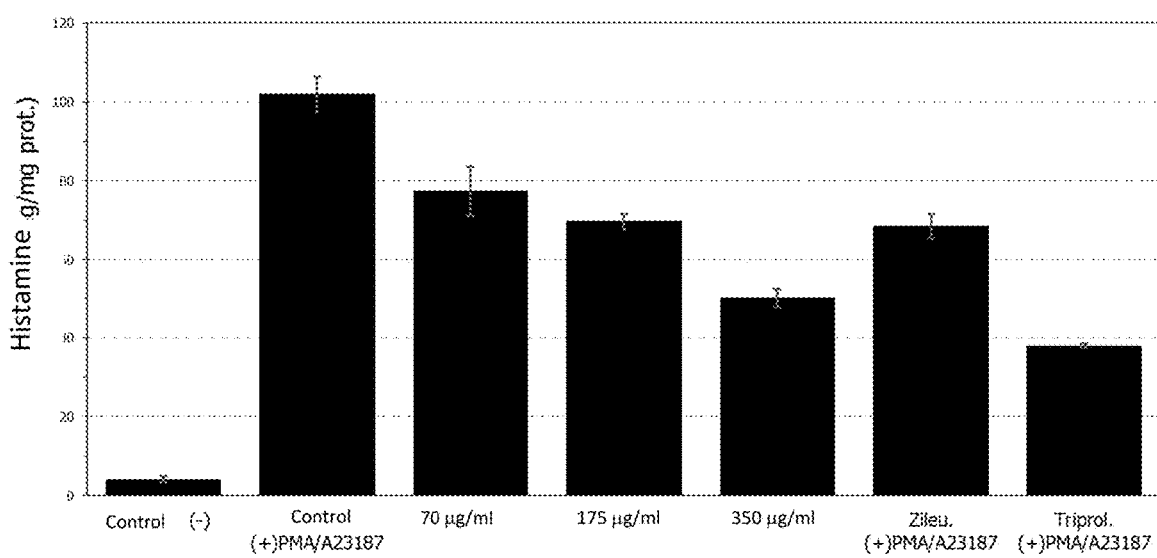
FIG. 6 shows the anti-allergic effect by measuring the release of histamine and C4 leukotriene, in particular the production of histamine by activated mast cells (FIG. 6A) and the production of LTC4 by activated mast cells (FIG. 6B).

The results presented in FIG. 6A demonstrate that the aqueous extract of Cleome droserifolia induces a clear dose-dependent inhibitory effect with respect to the secretion of histamine. The differences are −25% at the concentration of 70 µg/ml, −33% at the concentration of 175 µg/ml and −53% at the concentration of 350 µg/ml.

Figure 6B:
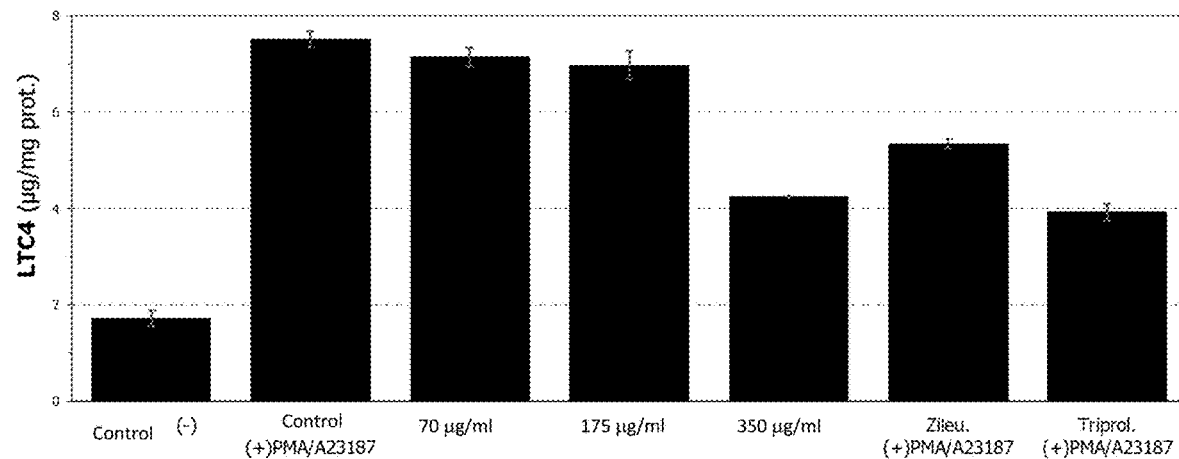

The results presented in FIG. 6B demonstrate that the aqueous extract of Cleome droserifolia according to the invention exhibits a significant inhibitory effect in a dose-dependent manner for the secretion of the inflammatory mediator Leukoitriene C4. This effect is statistically significant at 175 µg/ml, reducing the rate of secretion of the inflammatory mediator by 9% with $p \leq 0.05$ according to Student's test. At 350 µg/ml, the inhibition of the inflammatory mediator Leukotriene C4 collapses to −56% relative to the control with a statistical significance of p≤0.01 according to Student's test and in comparison to the PMA/A13187 control.

Thus, this test on a model of "activated" murine mast cells demonstrates that the aqueous extract of *Cleome droserifolia* can be used to treat skin inflammations. The extract according to the invention can thus be used as a cutaneous anti-inflammatory and anti-allergic agent.

Evaluation of the Anti-Inflammatory Effect of an Extract According to the Invention by Measuring the Release of Interleukin 6 and Interleukin 8 as Well as of the Secretion of Filaggrin.

The objective of this study is to evaluate the modulatory effects of an extract of *Cleome droserifolia* (dry aqueous extract of *Cleome droserifolia* in lyophilized form according to the invention) with respect to the inflammatory secretome of HaCaT keratinocytes activated by TNF-α/IFN-γ. After incubation, the levels of Interleukin 6 (IL-6), of Interleukin 8 (IL-8), of chemokine derived from macrophages as well as the level of filaggrin were thus measured. The extract according to the invention was used at 3 different non-toxic concentrations: C1=0.3 mg/ml; C2=0.75 mg/ml and C3=1.5 mg/ml. The results were compared with the negative control (TNF-α/IFN-γ) as well as with the epicatechin gallate positive control used at 10 μM and with the control not induced by inflammatory agents. For each operating condition, 3 wells were used.

The production of cytokines (IL-6 and IL-8) and of the MDC chemokine were measured in the culture media, 24 hours after induction of inflammatory stress by addition of TNF-α (10 ng/ml)/IFN-γ (10 ng/ml). The HaCaT cells were treated with the aqueous extract of *Cleome droserifolia*, before (24 h) and during (24 h) the TNF-α/IFN-γ stress. Filaggrin levels were measured in cell extracts.

IL-6 production: the amount of IL-6 produced was measured in the culture incubation media after stimulation with TNF-α/IFN-γ. IL-6 was quantified by the Elisa technique with an "IL-6 human High sensitivity Elisa kit" (ENZO Life Sciences) by measuring the absorbance at 450 nm. The mean absorbances were calculated. The IL-6 concentration of the samples was determined from the equation of the regression line of the calibration range (log[IL-6] versus log[O.D.]).

IL-8 production: the amount of IL-8 produced was measured in the culture incubation media after stimulation with TNF-α. IL-8 was quantified by the Elisa technique with a "Quantikine Elisa human IL-/CXCL8" assay kit (R&D Systems) by measuring the absorbance at 450 nm. The mean of the absorbances of the replicates (n=3), corrected by subtraction from that of the zero standard (Std0), was calculated. The IL-8 concentration of the samples was determined from the equation of the regression line of the calibration range (log[IL-8] versus log[O.D.]).

MDC (Macrophage-Derived Chemokine) production: the amount of MDC produced was measured in the culture incubation media after stimulation with TNF-α/IFN-γ. MDC was quantified by the Elisa technique with a "Quantikine Elisa human MDC" assay kit (R&D SYSTEMS) by measuring the absorbance at 450 nm. The mean of the absorbances of the replicates (n=3), corrected by subtraction from that of the zero standard (Std0), was calculated. The MDC concentration of the samples was determined from the equation of the regression line of the calibration range (log[MDC] versus log[O.D.]).

Filaggrin (FLG): the level of filaggrin was measured in cell extracts from cultures after stimulation with TNF-α/IFN-γ. FLG was quantified by the Elisa technique with a "human Filaggrin (FLG) Elisa kit" (CUSABIO) by measuring the absorbance at 450 nm. The mean of the absorbances of the replicates (n=3), corrected by subtraction from that of the zero standard (Std0), was calculated. The FLG concentration of the samples was determined from the equation of the regression line of the calibration range (log[FLG] versus log[D.O.]).

Figure 7A:
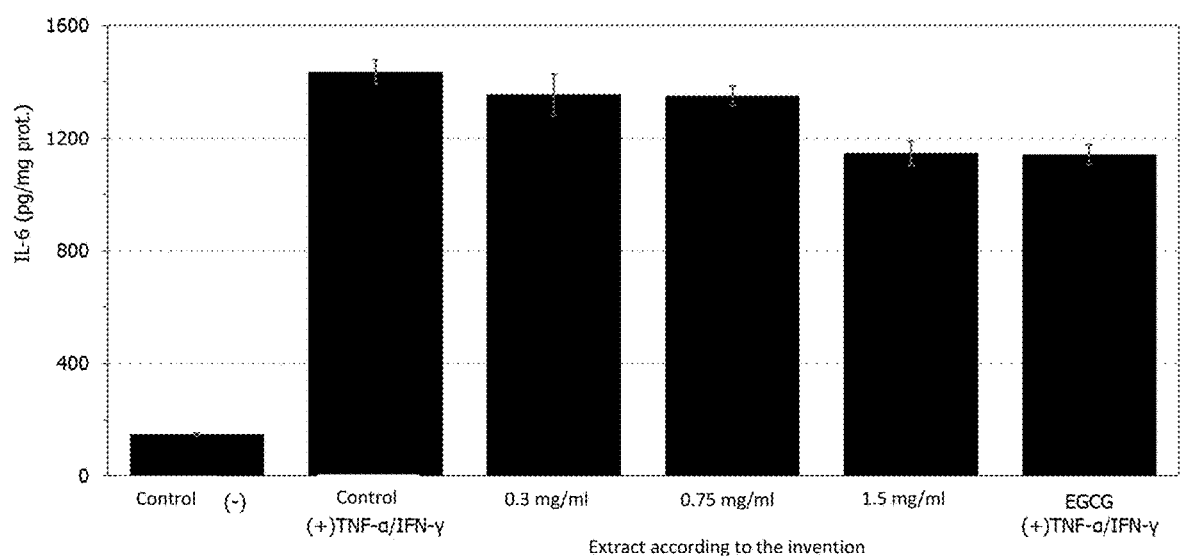
FIG. 7 shows the anti-inflammatory effect by measuring IL-6 (FIG. 7A), IL-8 (FIG. 7B) release, MDC production (FIG. 7C) and filaggrin secretion (FIG. 7D).

The results presented in FIG. 7A demonstrate a dose-dependent inhibitory effect of the extract according to the invention with respect to the secretion of IL-6 and in comparison with the negative control.

Figure 7B:
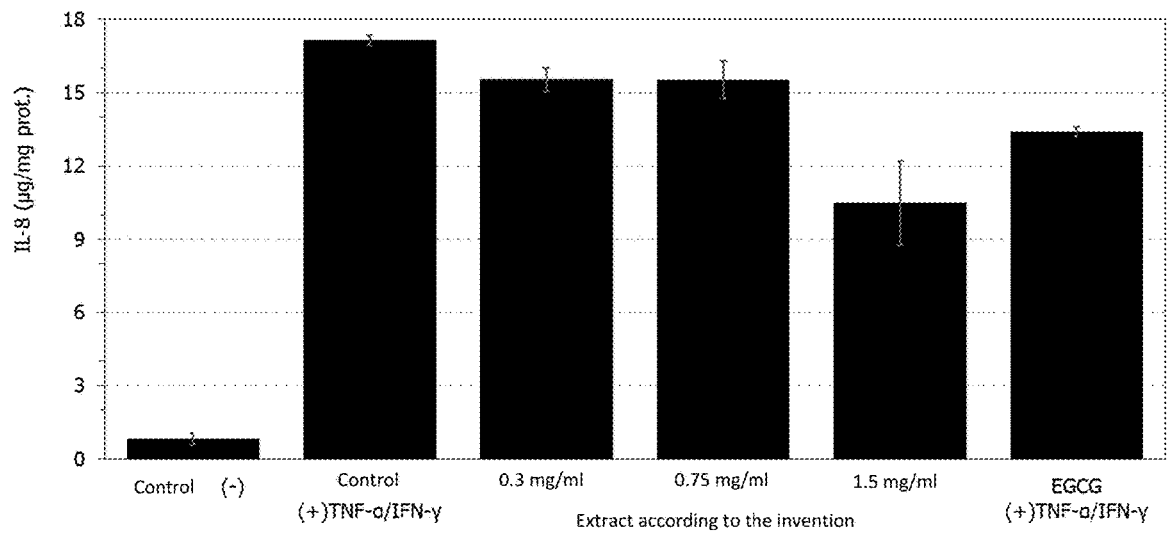

The results presented in FIG. 7B demonstrate a dose-dependent inhibitory effect of the extract according to the invention with respect to the secretion of IL-8.

Figure 7C:
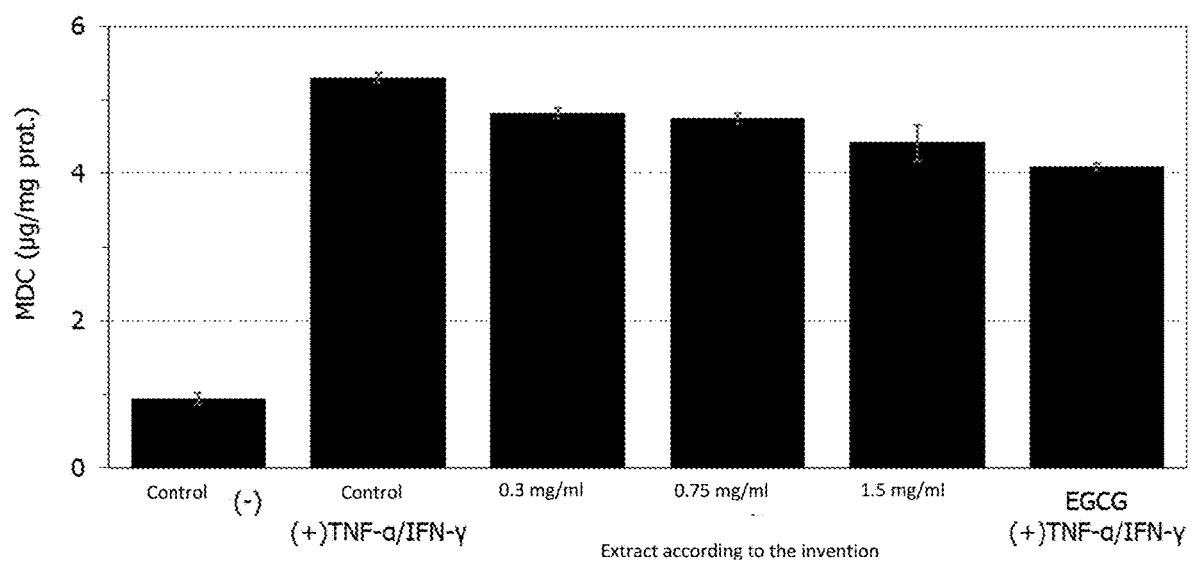

The results presented in FIG. 7C demonstrate a dose-dependent inhibitory effect of the extract according to the invention with respect to the secretion of MDC.

Figure 7D:
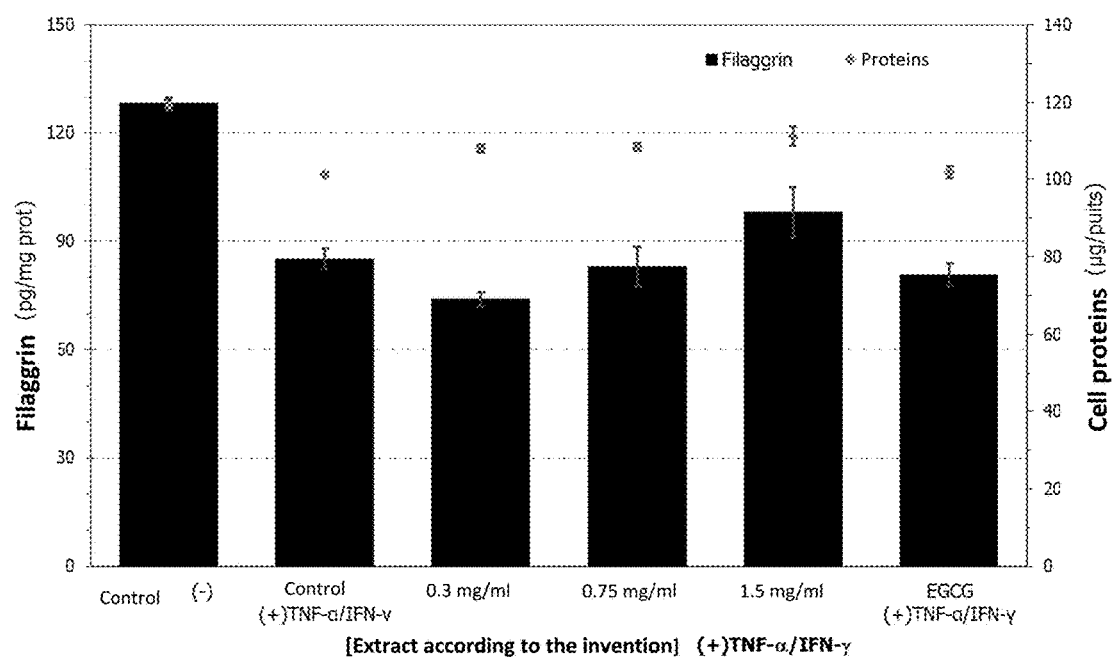

The results of the test presented in FIG. 7D show that the inflammatory stress TNF-α/IFN-γ (dose 10 ng/ml) induces a drop in the level of intracellular filaggrin. The basal level of FLG is statistically reduced by 34% (p≤0.01, Student's test) after TNF-α/IFN-γ stress. The level of FLG recorded after TNF-α/IFN-γ stress in the cultures treated with the extract according to the invention at C3 is higher than that observed in the positive control EGCG (+)TNF-α/IFN-γ. This result indicates that the treatment of the cells with the extract according to the invention makes it possible to restore the expression of filaggrin depressed by TNF-α/IFN-γ. A 15% increase in FLG was observed in comparison with the positive control wells (EGCG).

Thus, these results demonstrate that the extract according to the invention can be used as an anti-inflammatory and anti-allergic product but also as a skin hydration product and as a barrier function.

Evaluation of the Modulating Effect on the Allergic Inflammatory Secretome of the Epidermis Activated by PPI.

The skin anti-inflammatory potential of an extract of *Cleome droserifolia* (dry aqueous extract of *Cleome droserifolia* in lyophilized form according to the invention) was studied using the model of reconstructed human epidermis EpiDerm™ (MatTek) after activation of a Th2 atopic dermatitis-type inflammatory stress induced by a PPI mix [cytokine IL-1☐ at 60 ng/ml; +Poly(I:C) ligand at 10 μg/ml; +Pam3CSK4 ligand at 5 μg/ml+cytokines IL-4+IL-13 at 50 ng/ml each].

The evaluation of the anti-inflammatory potential was based on the measurement of the production and secretion by keratinocytes in the EpiDerm™ model of pro-inflammatory Interleukins 6 (IL-6) and 8 (IL-8) and of thymic stromal lymphopoietin (TSLP) in the culture media, after an inflammatory stress induced by the PPI mix and in the presence or in the absence of the preparation.

The tissues were pretreated with the test element by topical application, 24 hours before induction of the allergic inflammatory stress induced by the addition of the PPI mix in the tissue incubation medium. A second topical application of the test item was made to the activated EpiDerm tissues and the tissues were incubated for 48 hours before measuring IL6, IL8 and TSLP in the culture media.

The extract according to the invention was tested for its effectiveness at three concentrations in topical application after dilution of a stock solution in distilled water. These concentrations were defined so as not to exceed one twelfth of the maximum concentration tested during the acceptability studies of the preparation on the EpiDerm model, which was 18 mg/ml. The efficacy concentrations tested were:

C1=0.3 mg/ml; C2=0.75 mg/ml and C3=1.5 mg/ml. For each test condition, three wells of 0.6 cm² EpiDerm tissue were used.

The crude levels of IL-6 (pg/ml), IL-8 (pg/ml) and TSLP (pg/ml) were deduced by interpolation from the respective standard curves, then weighted by the viability of the tissues determined by the MTT test for each of the wells used during the efficacy test.

The results were expressed in arbitrary units (pg cytokine/DOMTT) and as a percentage relative to the IPP control (+) not treated with the product. The level of cytokines induced by the IPP control (+) was calculated according to the formula:

$$Cytok_{induct(+)IPP} - Cytok_{(-)IPP-}$$

Figure 9A:
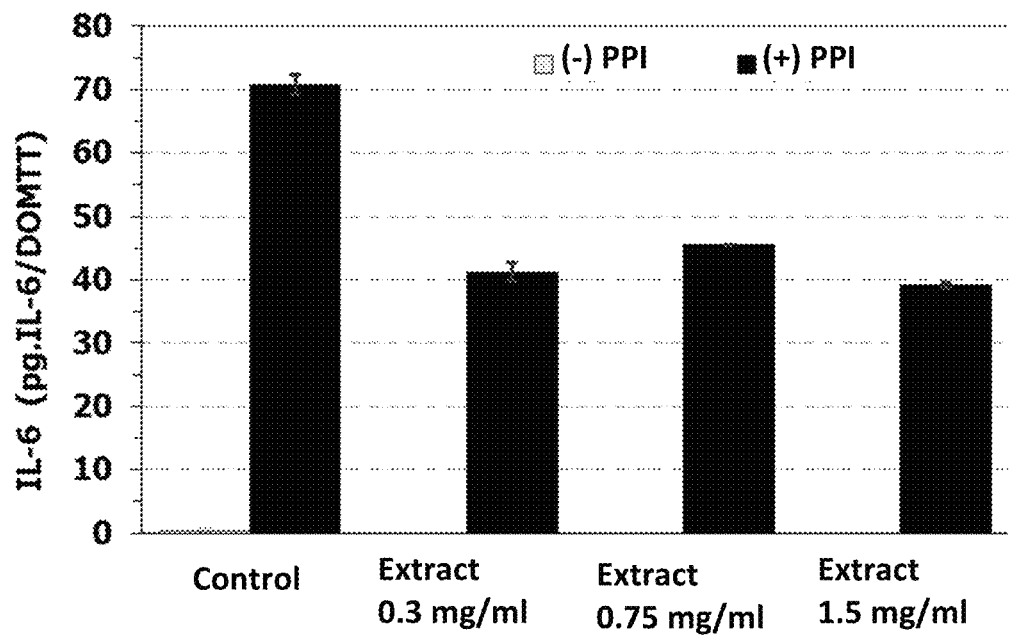
FIG. 9 shows the modulating effect on the allergic inflammatory secretome of the epidermis activated by PPI. The evaluation of the anti-inflammatory potential is based on the measurement of the production and secretion by the keratinocytes in the EpiDerm™ model of Interleukins 6 (FIGS. 9A and 9B) and IL-8 (FIGS. 9C and 9D) pro-inflammatory and thymic stromal lymphopoietin (TSLP) (FIGS. 9E and 9F) in the culture media, after an inflammatory stress induced by the PPI mix and in the presence or in the absence of the composition.
Figure 9B:
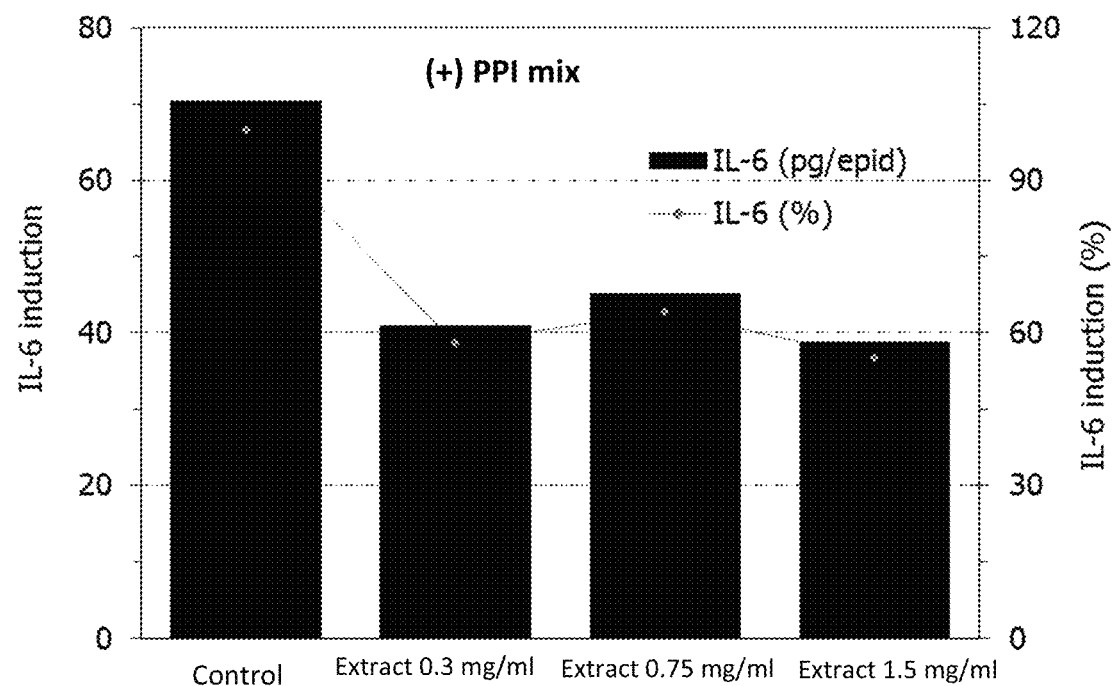

IL-6 production: The results in FIGS. 9A and 9B show that the extract of *Cleome droserifolia* according to the invention exhibits an inhibitory effect with respect to the secretion of IL-6.

Figure 9C:
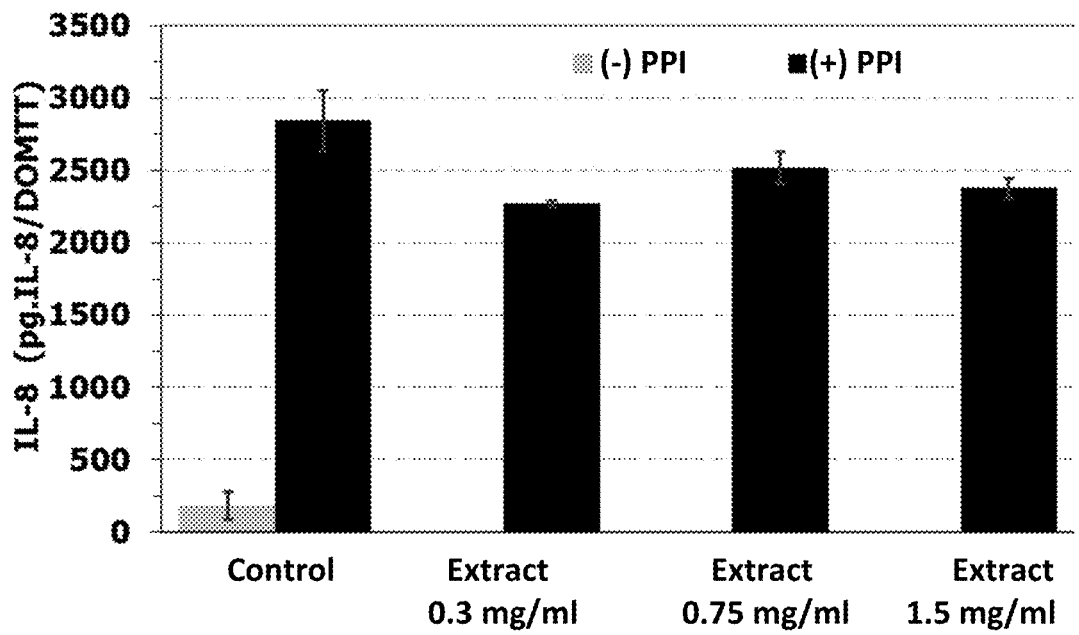
Figure 9D:
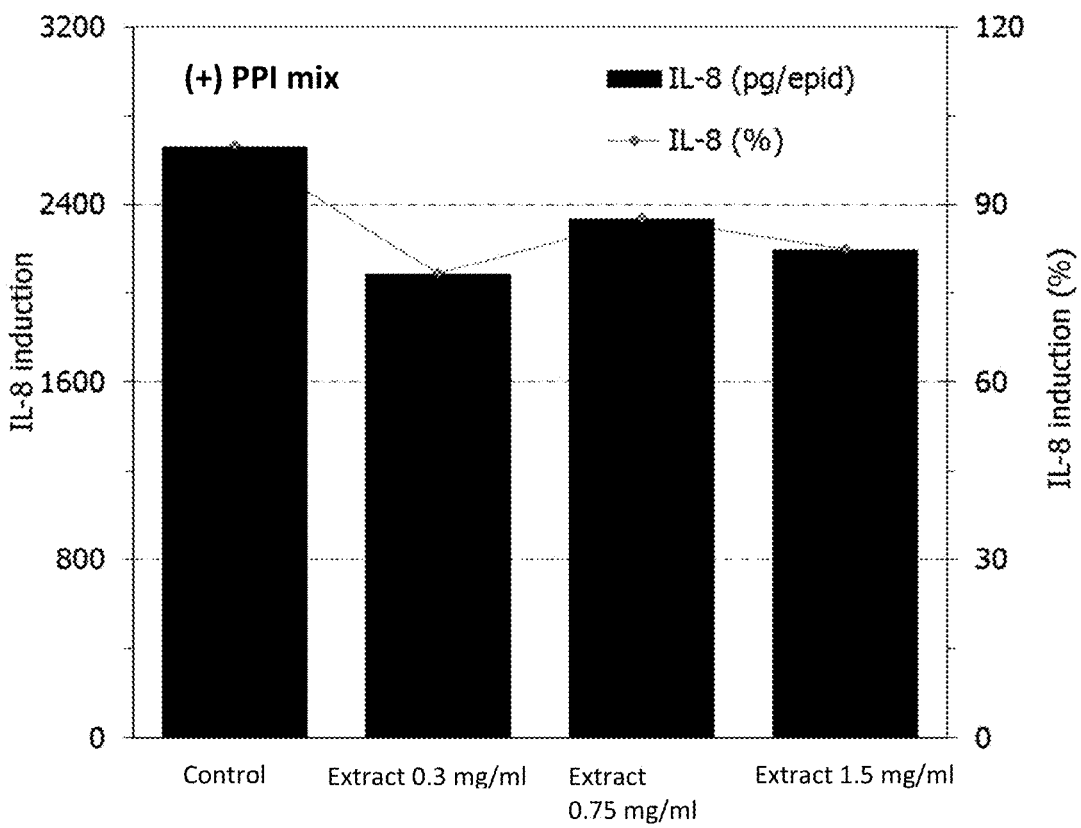

IL-8 production: The results in FIGS. 9C and 9D show that the extract of *Cleome droserifolia* according to the invention exhibits an inhibitory effect with respect to the secretion of IL-8.

Figure 9E:
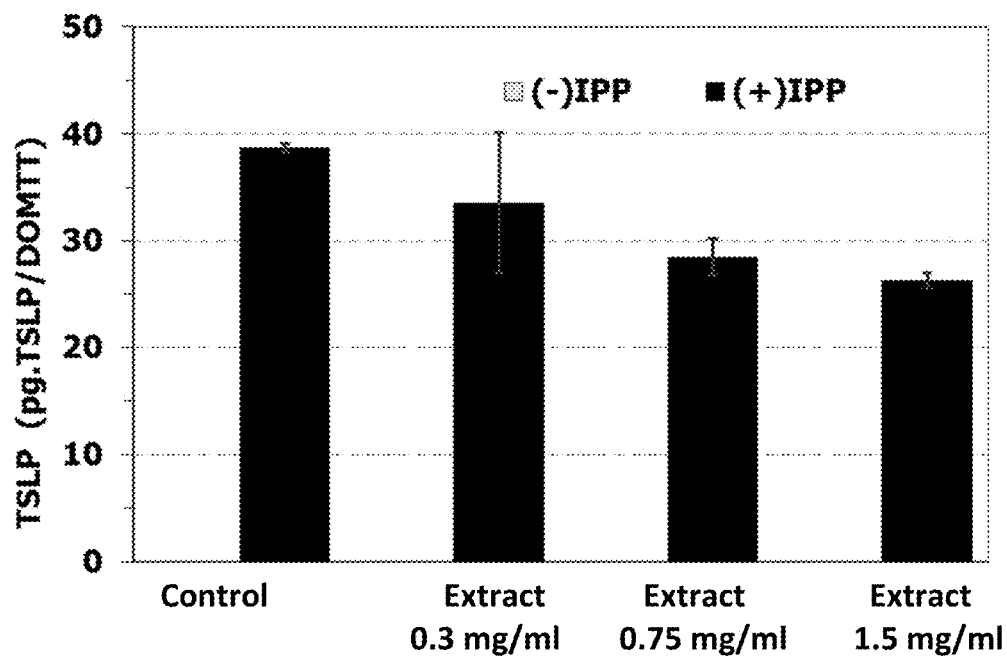
Figure 9F:
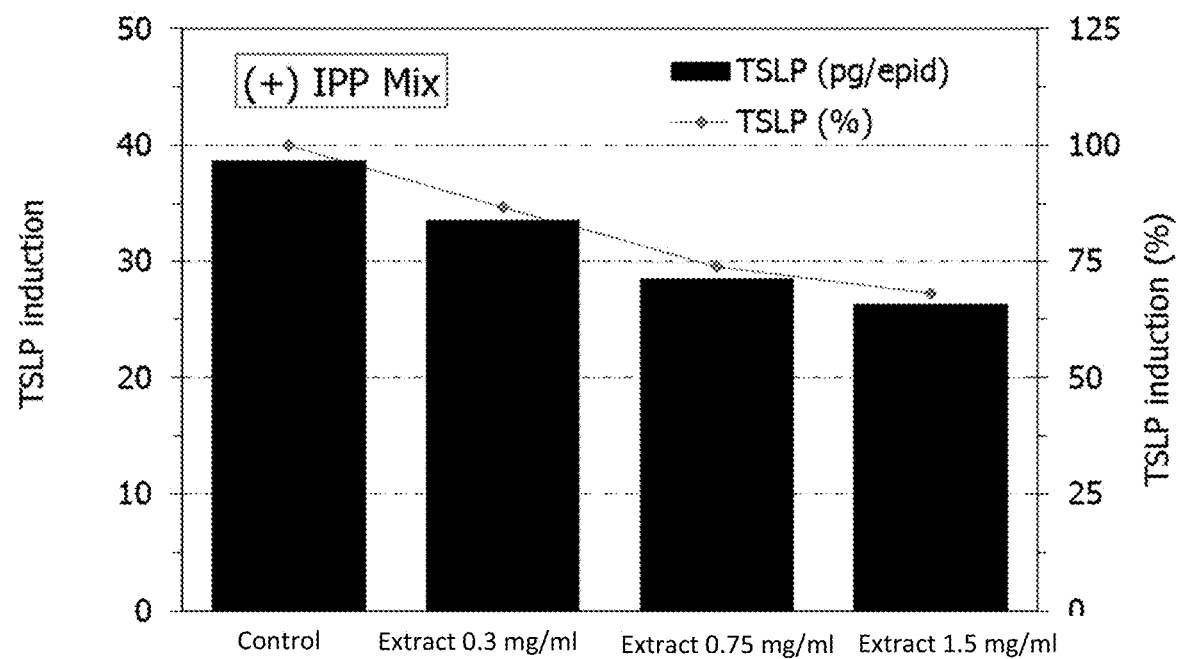

TSLP production: The results in FIGS. 9E and 9F show that the extract of *Cleome droserifolia* according to the invention exhibits a dose-dependent inhibitory effect with respect to the secretion of TSLP.

Thus, the extract according to the invention can be used in the treatment of skin diseases, such as, in particular, atopic dermatitis, skin allergy, rash, skin inflammation and eczema.

Test for demonstrating the cutaneous acceptability of the extract of *Cleome droserifolia* according to the invention on a model of reconstructed human skin.

The test was carried out on EpiDerm EP1-201 tissues with a surface area of 0.6 cm2 according to the method described previously (Ref. Bernard, M., et al. J. Pathol. 2017; 242: 234-235).

Briefly, an extract of *Cleome droserifolia* (dry aqueous extract of *Cleome droserifolia* in lyophilized form according to the invention) was diluted in distilled water in order to obtain a concentration of 3 mg/ml, 9 mg/ml and 18 mg/ml. After treatment at a rate of 50 µl/culture well, the tissues were incubated for 24 hours with the aqueous extract applied. A second application was made after 24 hours, then the tissues were incubated for an additional 72 hours. The control group was treated with an application of distilled water. For each concentration of the product and for the control group, 2 wells were used. Tissue viability was achieved by the MTT method.

Figure 8:
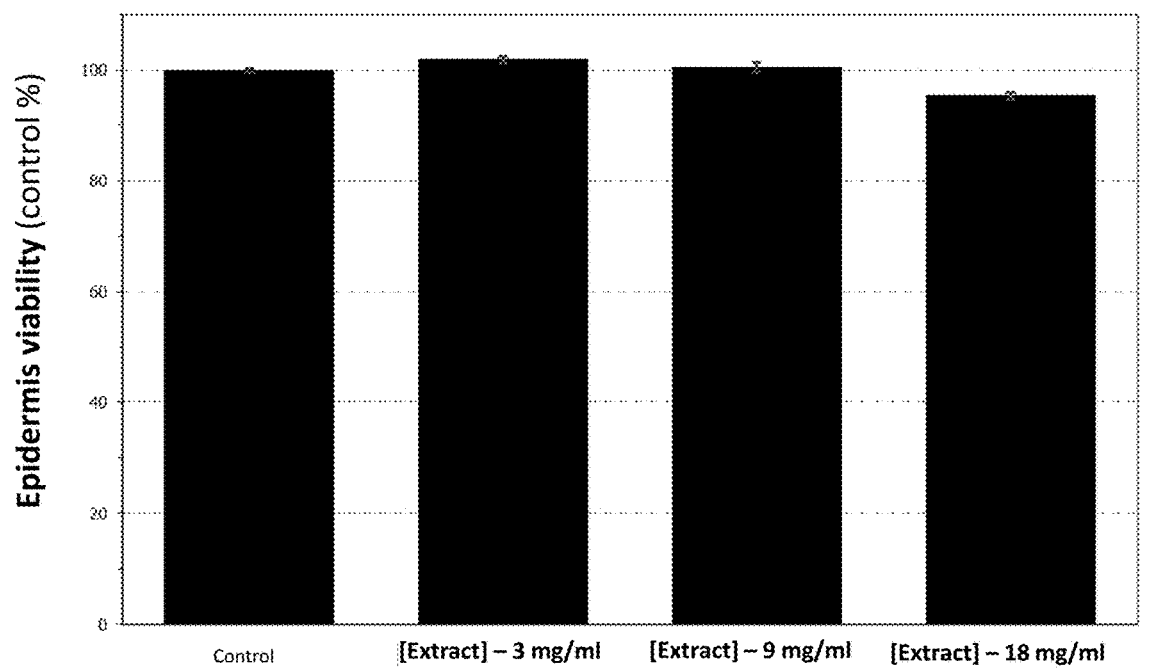
FIG. 8 shows the skin tolerance of the composition according to the invention on a model of reconstructed human skin.

The results presented in FIG. 8 make it possible to demonstrate the very good cutaneous acceptability of the extract of *Cleome droserifolia* according to the invention. Indeed, no significant modification of the viability of the tissues was recorded after topical application of the extract according to the invention.

The invention claimed is:

1. A method of treating skin and/or mucous membranes in a subject, wherein the method consists of:
   topically applying to the skin and/or mucous membranes of the subject a *Cleome droserifolia* extract or a composition comprising the *Cleome droserifolia* extract, wherein the *Cleome droserifolia* extract being obtained by: 1) extraction with water alone, 2) extraction with a mixture of 60 to 80 wt % water and 20 to 40 wt % alcohol or organic solvent; or 3) extraction with supercritical $CO_2$; and
   wherein the treatment is not for treating skin burns.

2. The method of claim 1, wherein the composition comprises at least 0.1% by weight of the *Cleome droserifolia* extract and/or wherein the *Cleome droserifolia* extract comprises *Cleome droserifolia* aerial parts.

3. The method of claim 1, wherein applying the *Cleome droserifolia* extract or the composition to the skin and/or mucous membranes has an anti-coagulant and/or anti-bleeding and/or healing and/or antioxidant and/or anti-inflammatory and/or anti-itching and/or anti-bacterial and/or anti-histamine and/or anti-allergic effect on the skin and/or mucous membranes.

4. The method of claim 1, wherein the method treats a pathology of the skin and/or mucous membranes.

5. The method of claim 4, wherein the pathology has an inflammatory and/or atopic profile having a Th1 and/or Th17 and/or Th2 cytokine profile.

6. The method of claim 4, wherein the pathology includes one or more of the following: urticaria, an infection of the skin and/or mucous membranes, a fungal infection of the skin and/or mucous membranes, atopic dermatitis, psoriasis, acne, rosacea, herpes, a canker sore, an insect bite, a sunburn, a rash and/or sore.

7. The method of claim 1, wherein the *Cleome droserifolia* extract is not an essential oil.

8. The method of claim 1, wherein the *Cleome droserifolia* extract is in liquid form.

9. The method of claim 1, wherein the *Cleome droserifolia* extract is in the form of a resinous gum soluble in water or of a lyophilizate soluble in water.

10. The method of claim 1, wherein the *Cleome droserifolia* extract or the composition is applied on healthy skin for an anti-aging and/or anti-redness cosmetic effect.

11. The method of claim 1, wherein the composition is in the form of a cream, an ointment, a gel, a paste, a lotion, an unguent, a toothpaste, a soap, a mouthwash, a shampoo, or a shaving foam.

* * * * *